US006114115A

United States Patent [19]
Wagner, Jr.

[11] Patent Number: 6,114,115
[45] Date of Patent: *Sep. 5, 2000

[54] USE OF IMMOBILIZED MISMATCH BINDING PROTEIN FOR DETECTION OF MUTATIONS AND POLYMORPHISMS, AND ALLELE IDENTIFICATION

[75] Inventor: Robert E. Wagner, Jr., Laporte, Colo.

[73] Assignee: ValiGene Corporation, New York, N.Y.

[*] Notice: This patent is subject to a terminal disclaimer.

[21] Appl. No.: 08/431,081

[22] Filed: Apr. 28, 1995

Related U.S. Application Data

[63] Continuation-in-part of application No. 08/147,785, Nov. 4, 1993.

[51] Int. Cl.[7] .............................. C12Q 1/68; C12P 19/34
[52] U.S. Cl. ............................................. 435/6; 435/91.2
[58] Field of Search ..................... 435/6, 91.2; 935/77, 935/78

[56] References Cited

U.S. PATENT DOCUMENTS

| | | | |
|---|---|---|---|
| 5,556,750 | 9/1996 | Modrich | 435/6 |
| 5,750,335 | 5/1998 | Gifford | 435/6 |

OTHER PUBLICATIONS

Lishamskaya et al. Am J Hum Genet 51:A385 (Oct. 1992).
Nelson et al. Nature Genetics 4:11–19 (May 1993).
Jiricny, J. et al., "Mismatch–containing oligonucleotide duplexes bound by the *E.coli* mutS–encoded Protein", *Nucl. Acids Res.* 16:7843–7853 (1988).
Su, S.S. et al., "Mispair Specificity of Methyl–directed DNA Mismatch Correction *in Vitro*", *J. Biol. Chem.* 263:6829–6835 (1988).
Lu, A.S. et al., "Detection of Single DNA Base Mutations with Mismatch Repair Enzymes", *Genomics* 14:249–255 (1992).
Lishanskaya, A. et al. (*Human Genet.* 51 (4 Suppl):A385, abstract #1517 (1992).
Lishanski, A. et al., "Mutation detection by mismatch binding protein, MutS, in amplified DNA:Application to the cystic fibrosis gene", *Proc. Natl. Acad. Sci. USA* 91:2674–2678 (1994 Mar.).
Modrich, P., "Methyl–directed DNA Mismatch Correction", *J. Biol. Chem.* 264:6597–6600 (1989).
Fazakerley et al., "Structures of mismatched base pairs in DNA and their recognition by the *Escherichia coli* mismatch repair system", EMBO J. 5:3697–3703 (1986).
Dohet, C. et al., "Large non–homology in heteroduplex DNA is processed differently than single base pair mismatches", *Mol. Gen. Genet.* 206:181–184 (1987).
Jones, M. et al., "Repair of a Mismatch Is Influenced by the Base Composition of the Surrounding Nucleotide Sequence", *Genetics* 115:605–610 (1987).
Lu, A.L. et al., "Repair of Single Base–Pair Transversion Mismatches of *Escherichia coli in Vitro:* Correction of Certain A/G Mismatches Is Independent of *dam Methylation* and Host mutHLS Gene Functions", *Genetics* 118:593–600 (1988).

Haber L.T. et al., "Nucleotide Sequence of the *Salmonella typhimurium mutS* Gene Required for Mismatch Repair: Homology of MutS and HexA of *Streptococcus pneumoniae*", *J. Bacteriol.* 170:197–202 (1988).
Pang, P.P. et al., "Identification and Characterization of the mutL and mutS Gene Products of *Salmonella typhimurium* LT2", *J. Bacteriol.* 163:1007–1015 (1985).
Priebe S.D. et al., "Nucleotide Sequence of the hexA Gene for DNA Mismatch Repair in *Streptococcus pneumoniae* and Homology of hexA to mutS of *Escherichia coli* and *Salmonella typhimurium*", *J. Bacteriol.* 170:190–196 (1988).
Valle G. et al., "The Sequence of a 6.3 kb Segment of Yeast Chromosome III Reveals an Open Reading Frame Coding for a Putative Mismatch Binding Protein", 1991 *Yeast* 7:981–988.
Miret J.J. et al., "Characterization of a DNA Mismatch–binding Activity in Yeast Extracts", 1993, *J. Biol Chem.* 268:3507–3513.
Stephenson, C. et al., "Selective Binding to DNA Base Pair Mismatches by Proteins from Human Cells", 1989, *J. Biol. Chem.* 264:21177–21782.
Karran, P. et al., "Mismatch binding proteins and tolerance to alkylating agents in human cells", 1990, *Mutat. Res.* 236:269–275.
Hughes M.J. et al., "The Purification of a Human Mismatch–binding Protein and Identification of Its Associated ATPase and Helicase Activities", 1992, *J. Biol. Chem.* 267:23876–23882.
Reenan, A.G. et al., "Isolation and Characterization of Two *Saccharomyces cerevisiae* Genes Encoding Homologs of the Bacterial HexA and MutS Mismatch Repair Proteins", 1993, *Genetics* 132:963–973.
Reenan, A.G. et al. "Characterization of Insertion Mutations in the *Saccharomyces cerevisiae* MSH1 and MSH2 Genes: Evidence for Separate Mitochondrial and Nuclear Functions", 1993, *Genetics* 132:975–985.

(List continued on next page.)

*Primary Examiner*—Carla J. Myers
*Assistant Examiner*—Diana Johannsen
*Attorney, Agent, or Firm*—Pennie & Edmonds LLP

[57] ABSTRACT

A method for detecting mutations, such as a single base change or an addition or deletion of about one to four base pairs, is based on the use of an immobilized DNA mismatch-binding protein, such as MutS, which binds to a nucleic acid hybrid having a single base mismatch or unpaired base or bases, thereby allowing the detection of mutations involving as little as one base change in a nucleotide sequence. Such a method is useful for diagnosing a variety of important disease states or susceptibilities, including the presence of a mutated oncogene and the presence of DNA containing triplet repeat sequences which characterize several genetic diseases including fragile X syndrome. The present method is used to isolate or remove by affinity chromatography duplex DNA molecules containing mismatches such as error-containing molecules in PCR-amplified DNA samples. Also provided are compositions and kits useful for practicing the methods of the present invention.

20 Claims, 14 Drawing Sheets

OTHER PUBLICATIONS

Fishel, R. et al., "Purified Human MSH2 Protein Binds to DNA Containing Mismatched Ducleotides", *Cancer Res.* 54:5539–5542 (Nov. 1, 1994).

Fishel, R. et al., "Binding of Mismatched Microsatellite DNA Sequences by the Human MSH2 Protein", *Science* 266:1403–1405 (Nov. 25, 1994).

Fishel, R. et al., "The Human Mutator Gene Homolog MSH2 and Its Association with Hereditary Nonpolyposis Colon Cancer", *Cell* 75:1027–1029 (1993).

Leach, S.S. et al., "Mutations of a mutS Homolog in Hereditary Nonpolyposis Colorectal Cancer", *Cell* 75:1212–1225 (1993).

New et al., "The Yeast gene MSH3 defines a new class of eularyotic MutS homologues", *Mol. Gen. Genet.* 239:97–108 (1993).

Shimada, T. et al., "A 165–Base Pair Sequence Between the Dihydrofolate Reductase Gene and the Divergently Transcribed Upstream Gene is Sufficient for Bidirectional Transcriptional Activity", *J. Biol. Chem.* 264: (1989) p. 20171–20174.

Linton, J. et al., "Dual Bidirectional Promoters at the Mouse dhfr Locus: Cloning and Characterization of Two mRNA Classes of the Divergently Transcribed Rep–1 Gene", *Molec. Cell. Biol.* 7:3058–3072 (1989).

Fujii, H. et al., "Isolation and Characterization of cDNA Clones Derived from the Divergently Transcribed Gene in the Region Upstream from the Human Dihydrofolate Reductase Gene", *J. Biol. Chem.* 264:10057 (1989) p. 10057–10064.

Bowen, B. et al., "The Detection of DNA–Binding Proteins by Protein Blotting", *Nucl. Acids Res.* 8:1–20 (1979).

Miskimins, W.K. et al., "Use of a Protein–Blotting Procedure and a Specific DNA Probe to Identify Nuclear Proteins that Recognize the Promoter Region of the Transferrin Receptor Gene", *Proc. Natl. Acad. Sci. USA* 82:6741–6744 (1985).

Keller, A.D. et al., "Selection of Sequences Recognized by a DNA Binding Protein Using a Preparative Southwestern Blot", *Nucl. Acids Res.* 19:4675–80 (1991).

Norby, P.L. et al., "Determination of Recognition–Sequences for DNA–Binding Proteins by a Polymerase Chain Reaction Assisted Binding Site Selection Method (BSS) Using Nitrocellulose Immobilized DNA Binding Protein", *Nucl. Acids Res.* 20:6317–6321 (1992).

Singh et al., "Molecular Cloning of an Enhancer Binding Protein: Isolation by Screening of an Expression Library with a Recognition Site DNA", *Cell* 52:415–423 (1988); Singh et al., *Bio Techniques* 7:253–261 (1989).

Vinson et al., "In Situ Detection of Sequence–Specific DNA Binding Activity Specified by a Recombinant Bacteriophage", *Genes & Devel.* 2:801–806 (1988).

Oliphant, A.R. et al., "Defining the Sequence Specificity of DNA–Binding Proteins by Selecting Binding Sites from Random–Sequence Oligonucleotides: Analysis of Yeast GCN4 Protein", *Molec. Cell. Biol.* 9:2944–2949 (1989).

Perrino, F.W. et al., "Interaction of a Folded Chromosome–Associated Protein With Single–Stranded DNA–Binding Protein of *Escherichia coli*, Identified by Affinity Chromatography", *J. Biol. Chem.* 263:11833–11839 (1988).

Meyer, R.R. et al., "The Single–Stranded DNA–Binding Protein of *Escherichia coli*", *Microbiol. Rev.* 54:342–380 (1990).

Bhattacharya, N.P. et al., "Mutator phenotypes in human colorectal carcinoma cell lines", *Proc. Natl. Acad. Sci. USA* 91:6319–6323 (1994).

Bronner, E.C. et al., "Mutation in the DNA mismatch repair gene homologue hMLH 1 is associated with hereditary non–polyposis colon cancer", *Nature* 368, 258–261 (1994).

Parker, B.O. et al., "Repair of DNA heteroduplexes containing small heterologous sequences in *Escherichia coli*", *Proc. Natl. Acad. Sci. USA* 89:1730–1734 (1992).

Alani, E et al., "The *Saccharomyces cerevisiae* Msh2 protein specifically binds to duplex oligonucleotides containing mismatched DNA base pairs and insertions", Genes Dev. 9:234–247 (Jan. 15, 1995).

TRIPLET REPEAT DIAGNOSTIC

I. To detect repeat block larger than probe repeat block (Disease diagnostic):

Probe: (CCG or CAG repeat)

*BxxxxxxxxxCCGCCGCCGCCGCCGCCGCCGCCGCCGCCGCCGCCGCCGCCGnnnnnnnnn

Repeat block smaller than smallest block to be detected.

A. Test repeat block smaller than probe repeat block.

```
        xxxxxxxxxGGCGGCGGCGGCGGCGGCGGCGGCGGCGGCnnnnnnnnn    Test
       B*xxxxxxxxxCCGCCGCCGCCGCCGCCGCCGCCGCCGCCGnnnnnnnnn   Probe
                          CG
                        C    C
                       G      C
                       C      G
                       C      C
                        G    C
                          CCG
```

MutS does NOT recognize this duplex.

B. Test repeat block larger than probe repeat block:

```
                                      CG
                                      GG
                                      GC
                                      CG
                                      GG
                                      GC
                                      CG
                                      GG
                                      GC                                      Test
       xxxxxxxxxGGCGGCGGCGGCGGCGGCGGCGGCGGCGGCGGCGGCGGCGGCGGCnnnnnnnnn
      *BxxxxxxxxxCCGCCGCCGCCGCCGCCGCCGCCGCCGCCGCCGCCGCCGCCGnnnnnnnnnB*
                                                                       Probe
```

MutS DOES recognize this duplex.

FIG.12A

II. To detect repeat block smaller than probe repeat block:

Probe: (CGG or CTG repeat)

*BxxxxxxxxxCGGCGGCGGCGGCGGCGGCGGCGGCGGCGGCGGCGGCGGCGGnnnnnnnnnn

Repeat block larger than largest block to be detected.

A. Test repeat block smaller than probe repeat block.

xxxxxxxxxCCGCCGCCGCCGCCGCCGCCGCCGCCGnnnnnnnnnn  Test
  *BxxxxxxxxxGGCGGCGGCGGCGGCGGCGGCGGCGGCnnnnnnnnnn  Probe
          GC
          GG
          CG
          GC
          GG
          CG
          GC
          GG
          CG MutS DOES recognize this duplex.

B. Test repeat block larger than probe repeat block.

```
                G C C
              C       G
            C           C
             G        C
              C      G
               C    C
                GC              Test
xxxxxxxxxGCCGCCGCCGCCGCCGCCGCCGCCGCCGCCGCCGCCGCCGCCGCCnnnnnnnnnn
*BxxxxxxxxxCGGCGGCGGCGGCGGCGGCGGCGGCGGCGGCGGCGGCGGCGGnnnnnnnnnn
                                                            Probe
```

MutS does NOT recognize this duplex.

FIG. 12B

```
                         SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:1:

GCACCTGACT CCTGGGGAGA AGTCTGCCGT                                          30

(2) INFORMATION FOR SEQ ID NO:2:

(i) SEQUENCE CHARACTERISTICS:
         (B) TYPE: nucleic acid
         (C) STRANDEDNESS: single
         (D) TOPOLOGY: linear (xi) SEQUENCE DESCRIPTION: SEQ ID NO:2:

CGTGGACTGA GGACCCCTCT TCAGACGGCA                                          30

(2) INFORMATION FOR SEQ ID NO:3:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:3:

ACGGCAGACT TCTCCTCAGG AGTCAGGTGC                                          30

(2) INFORMATION FOR SEQ ID NO:4:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:4:

GCACCTGACT CCTGTGGAGA AGTCTGCCGT                                          30

(2) INFORMATION FOR SEQ ID NO:5:

(i) SEQUENCE CHARACTERISTICS:
         (A) LENGTH: 30 base pairs
         (B) TYPE: nucleic acid
```

```
            (C) STRANDEDNESS: single
            (D) TOPOLOGY: linear (xi) SEQUENCE DESCRIPTION: SEQ ID NO:5:

ACGGCAGACT TCTCCGCAGG AGTCAGGTGC                                              30

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:6:

GCACCTGACT CCTGCGGAGA AGTCTGCCGT                                              30

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:7:

GCACCTGACT CCTGAGGAGA AGTCTGCCGT                                              30

(2) INFORMATION FOR SEQ ID NO:8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:8:

ACGGCAGACT TCTCCACAGG AGTCAGGTGC                                              30

(2) INFORMATION FOR SEQ ID NO:9:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:9:

ACGGCAGACT TCTCCCCCAG GAGTCAGGTG C                                            31

(2) INFORMATION FOR SEQ ID NO:10:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:10:

ACGGCAGACT TCTCCACCCA GGAGTCAGGT GC                                           32

(2) INFORMATION FOR SEQ ID NO:11:

(i) SEQUENCE CHARACTERISTICS:
            (A) LENGTH: 33 base pairs
            (B) TYPE: nucleic acid
            (C) STRANDEDNESS: single
```

(D) TOPOLOGY: linear (xi) SEQUENCE DESCRIPTION: SEQ ID NO:11:

ACGGCAGACT TCTCCGACCC AGGAGTCAGG TGC                               33

(2) INFORMATION FOR SEQ ID NO:12:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:12:

ACGGCAGACT TCTCCGGACC CAGGAGTCAG GTGC                              34

(2) INFORMATION FOR SEQ ID NO:13:

(i) SEQUENCE CHARACTERISTICS:
            (A) LENGTH: 100 base pairs
            (B) TYPE: nucleic acid
            (C) STRANDEDNESS: double
            (D) TOPOLOGY: linear (xi) SEQUENCE DESCRIPTION: SEQ ID NO:13:

GCACTAACTT CAGGGTGATG CTGGTGAAGG TGGGAGAAGG TGAGGAGGGG CAGTGGAGCG    60

TGAAGACCAA ACACCAGATG ATGAGGTAGG GGCTCCTGCG                        100

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:14:

GCACTAACTT CAGGGTGATG                                              20

(2) INFORMATION FOR SEQ ID NO:15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:15:

GCGTCCTCGG GGATGGAGTA                                              20

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:16:

GAAGGTGATG AGACGGAT                                                18

(2) INFORMATION FOR SEQ ID NO:17:

(i) SEQUENCE CHARACTERISTICS:
            (A) LENGTH: 18 base pairs
            (B) TYPE: nucleic acid

```
            (C) STRANDEDNESS: single
            (D) TOPOLOGY: linear (xi) SEQUENCE DESCRIPTION: SEQ ID NO:17:

CCCAGGAGAT TCTGTCTC                                                        18
```

USE OF IMMOBILIZED MISMATCH BINDING PROTEIN FOR DETECTION OF MUTATIONS AND POLYMORPHISMS, AND ALLELE IDENTIFICATION

This application is a continuation-in-part of U.S. application Ser. No. 08/147,785, filed Nov. 4, 1993, the contents of which are herein incorporated by reference in their entirety.

BACKGROUND OF THE INVENTION

1. Field of the Invention

The invention in the fields of molecular biology and medicine relates to a method for detecting or screening for mutations or heterozygosity involving as little as one base change or a single base addition to, or deletion from, the wild-type DNA sequence, as well as methods for removing mismatch-containing DNA from batches of amplified DNA.

2. Description of the Background Art

Progress in human molecular and medical genetics depends on the efficient and accurate detection of mutations and sequence polymorphisms, the vast majority of which results from single base substitutions and small additions or deletions. Assays capable of detecting the presence of a particular mutation or mutant nucleic acid sequence in a sample are therefore of substantial importance in the prediction and diagnosis of disease, forensic medicine, epidemiology and public health. Such assays can be used, for example, to detect the presence of a mutant gene in an individual, allowing determination of the probability that the individual will suffer from a genetic disease. The ability to detect a mutation has taken on increasing importance in early detection of cancer or discovery of susceptibility to cancer with the discovery that discrete mutations in cellular oncogenes can result in activation of that oncogene leading to the transformation of that cell into a cancer cell (Nishimura, S. et al., *Biochem. J.* 243:313–327 (1987); Bos, J. L., *Cancer Res.* 49:4682–4689 (1989)).

The desire to increase the utility and applicability of such assays is often frustrated by assay sensitivity as well as complexity and cost. Hence, it would be highly desirable to develop more sensitive as well as simple and relatively inexpensive assays for detection of alterations in DNA.

Nucleic acid detection assays can be based on any of a number of characteristics of a nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents such as enzymes (Kourilsky et al., U.S. Pat. No. 4,581,333), radioisotopes (Falkow et al., U.S. Pat. No. 4,358,535; Berninger, U.S. Pat. No. 4,446,237), fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), and the like.

Most methods devised to attempt to detect genetic alterations consisting of one or a few bases involve hybridization between a standard nucleic acid (DNA or RNA) and a test DNA such that the mutation is revealed as a mispaired or unpaired base in a heteroduplex molecule. Detection of these mispaired or unpaired bases has been accomplished by a variety of methods. Mismatches have been detected by means of enzymes (RNaseA, MutY) which cut one or both strands of the duplex at the site of a mismatch (Myers, R. M. et al., *Cold Spring Harbor Symp. Quant. Biol.* 51:275–284 (1986); Gibbs, R. et al., *Science* 236:303–305 (1987); Lu, A. S. et al., 1992, *Genomics* 14:249–255 (1992)). Duplexes without mismatches are not cut. By using radioactively labeled nucleic acid fragments to anneal to a test DNA, it is possible to use these enzymes to generate specific size fragments when a mutation is present in the test DNA. The fragments are distinguished from uncut fragments by means of polyacrylamide gel electrophoresis (PAGE). The major problems with these methods are that they require the use of RNA (RNase method) or have the ability to detect only a limited number of mismatches (MutY method).

Mismatch-containing DNA duplexes have also been distinguished from perfectly matched duplexes by means of denaturing gel electrophoresis. In this system, duplexes are run in PAGE in a denaturing gradient under conditions where mismatch-containing DNA denatures more readily than the identical duplex lacking a mismatch, such that the two kinds of duplexes migrate differently. This method, while sensitive and accurate, is extremely laborious and requires a high level of technical sophistication.

Two other methods of mutation detection depend on the failure to extend or join fragments of DNA when mismatches are present. Both require the use of standard DNA oligonucleotides that end precisely at the site of the mutation in question such that, when annealed to test DNA, it is the last base of the oligonucleotide which is mismatched. Mismatch detection depends either on (a) the inability of DNA polymerase to extend an oligonucleotide with a mismatched terminal base or (b) the inability of DNA ligase to join two oligonucleotides when there is a mismatch at the joint between them. Fragment length is determined by gel electrophoresis. Presence of longer fragments than the input oligonucleotides indicates that a mismatch, i.e., mutation, was not present in the test DNA. These methods are also somewhat laborious, require that the exact location of the mutation be known and are difficult to interpret when the sample DNA is heterozygous for the mutation in question. Therefore, they are not practical for use in screening for polymorphisms.

A chemical method for cleavage of mismatched DNA (Cotton, R. G. et al., *Proc. Natl. Acad. Sci. USA* 85:4397–4401 (1988); Cotton, R. G., *Nuc. Acids Res* 17:4223–4233 (1989)) is based on chemical cleavage at a mismatch site in a DNA—DNA heteroduplex, using a number of agents, in particular osmium tetroxide and hydroxylamine. DNA probes are prepared by restriction enzyme cleavage of DNA of interest. Plasmid DNA containing the sequence of interest is hybridized to labeled probe DNA (either end-labeled or internally labeled with $^{32}P$). Hydroxylamine chemically modifies mismatched cytosines; osmium tetroxide modifies mismatched thymines. Piperidine is then used to cleave the DNA at the modified sites. PAGE and autoradiography are then used to identify the cleavage products. This method is said to have the advantage of detecting all possible single base pair mismatches because it results in cleavage at a matched base pair in the vicinity of a mismatch.

Publications from Caskey's laboratory (Caskey, C. T. et al., European Patent Publication 333,465 (Sep. 20, 1989); Grompe, M. et al., *Proc. Natl. Acad. Sci. USA* 86:5888–5892 (1989)) disclose a method for localizing a mutation which utilizes PCR-amplified cDNA as a source of template for the mismatch cleavage reaction. This technique was successfully applied in studying ornithine transcarbamoylase deficiency patients to map mutations.

Kung et al., U.S. Pat. No. 4,963,658, discloses detection of single stranded DNA (ssDNA) by binding with a high-affinity ssDNA-binding protein, such as a topoisomerase or a DNA unwinding protein which itself can be bound to a label such as β-D-galactosidase.

Wagner et al. PCT publication WO93/02216 shows that *E. coli* MutS, in solution, detects G//T, G//G and A//C mismatches as well as a frameshift mutation of +1 base. There is no disclosure of using immobilized MutS in this method.

(The symbol "//" is used hereinafter with nucleotide base designations to indicate mispaired bases. Properly paired bases are designated with a ":" for example G:C.)

Lishanskaya et al. (*Human Genet.* 51, (4 Suppl):A385, abstract #1517 (1992)) is an abstract disclosing the detection of heterozygotes for the amplified CFTR (cystic fibrosis) gene. The method was not shown to be useful for detecting single base mismatches, or mispairings of 1, 2 or 4 bases. Rather, the reference disclosed detection of a mutation causing a three base pair deletion using a gel mobility band-shift assay to detect MutS-heteroduplex complexes but did not suggests immobilizing a MBP.

Lishanski, A. et al., *Proc. Natl. Acad. Sci. USA* 91:2674–2678 (1994 March) reveals detection of frame shift mutations and A//C, G//T, G//A and T//C mismatches (most convincingly G//T) using MutS. The method worked poorly with duplexes containing single base pair mismatches. At the time that this paper was published, after the filing date of the priority application of this application, the authors were still trying to develop improved detection methods which utilized the methods that the present inventor had already invented and disclosed.

A number of publications describe methods for studying certain DNA binding proteins, in particular sequence-specific transcription factors, by electrophoretic separation (generally under denaturing conditions) of proteins, blotting ("Southwestern blots") or spotting of the separated proteins onto nitrocellulose filters, and probing of the filters with labeled DNA or oligonucleotide preparations. See, for example, Bowen, B. et al., *Nucl. Acids Res.* 8:1–20 (1979); Miskimins, W. K. et al., *Proc. Natl. Acad. Sci. USA* 82:6741–6744 (1985); Keller, A. D. et al., *Nucl. Acids Res.* 19:4675–80 (1991); Norby, P. L. et al., *Nucl. Acids Res.* 20:6317–6321 (1992)). Such initially denatured proteins must be renatured to perform their DNA binding functions; many proteins cannot be successfully renatured.

Similar approaches have been used to screen expression libraries by preparing protein replica filters and probing them with labeled DNA or oligonucleotides (Singh et al., *Cell* 52:415–423 (1988); Singh et al., *BioTechniques* 7:253–261 (1989); Vinson et al., *Genes & Devel.* 2:801–806 (1988)). Oliphant, A. R. et al. (*Molec. Cell. Biol.* 9:2944–2949 (1989)) reported use of a sequence-specific DNA binding protein (yeast GCN4 transcriptional activator) coupled to Sepharose to select DNA molecules containing binding sites for this protein from random sequence oligonucleotides.

Interactions of DNA with immobilized *E. coli* single stranded DNA-binding protein (SSB) has been reported (Perrino, F. W. et al., *J. Biol. Chem.* 263:11833–11839 (1988)) and is reviewed in Meyer, R. R. et al. (*Microbiol. Rev.* 54:342–380 (1990)).

3. Mismatch Repair Systems and Mismatch Binding Proteins

DNA mismatch repair systems employ a family of proteins including proteins which recognize and bind to mismatch-containing DNA, which are designated mismatch binding proteins (MBPs). For reviews, see Radman, M. et al., *Annu. Rev. Genet.* 20:523–538 (1986); Radman, M. et al., *Sci. Amer.*, August 1988, pp. 40–46; Modrich, P., *J. Biol. Chem.* 264:6597–6600 (1989)). The MutS protein was identified as such a component of the *E. coli* mismatch repair system. See, for example, Lahue, R. S. et al., *Science* 245:160–164 (1989); Jiricny, J. et al., *Nucl. Acids Res.* 16:7843–7853 (1988); Su, S. S. et al., *J. Biol. Chem.* 263:6829–6835 (1988); Lahue, R. S. et al., *Mutat. Res.* 198:37–43 (1988); Dohet, C. et al., *Mol. Gen. Genet.* 206:181–184 (1987); and Jones, M. et al., *Genetics* 115:605–610 (1987). Analogous proteins are known in other bacterial species including MutS in *Salmonella typhimurium* (Lu, A. L. et al., *Genetics* 118:593–600 (1988); Haber L. T. et al., *J. Bacteriol.* 170:197–202 (1988); Pang, P. P. et al., *J. Bacteriol.* 163:1007–1015 (1985)) and the hexA protein of *Streptococcus pneumoniae* (Priebe S. D. et al., *J. Bacteriol.* 170:190–196 (1988); Haber et al., supra).

Using a gel-shift assay (as well as a filter-binding assay), Jiricny et al. (supra) reported detection of G//T and G//A mismatches, whereas binding to an A//C mismatch was weak and C//C was undetectable.

Su et al. (supra) used a nuclease protection assay to detect binding of MutS to DNA. This reference showed that all the examined mismatches were bound, with binding to A//C, G//A, T//C and G//T mismatches being stronger than binding to A//G, C//T, and C//C mismatches.

Purified MutS protein binds DNA containing mispaired bases, but does not bind DNA without mismatches or single-stranded DNA. The MutS-DNA interaction does not result in any degradation or modification of the DNA. None of the above references disclose the possibility of using a MBP or immobilized MBP as part of a mutation detection assay or for purposes of removing mismatched DNA from amplified DNA samples.

The literature concerning DNA repair suggests that all mismatches are not repaired with equal efficiency in vivo (Dohet, C. et al., *Proc. Natl. Acad. Sci. USA* 82:503–505 (1985). If poorly-repaired mismatches were created as frequently as well-repaired mismatches, one would not observe the 100–1000-fold increase in mutation rate in mutant cells lacking MutS function. Therefore, the poorly-recognized mismatches, in particular C//C (Dohet et al., supra, Jiricny et al., supra), must not be created as frequently as other well-recognized mismatches, since 99.9% of created mutations are repaired. Hence, MutS must bind to mismatched DNA (and induce the repair process) for virtually any error made by a polymerase enzyme.

With the recent discoveries that mutations in genes coding for MBPs can lead to predisposition to may cancers, particularly colon cancers, there is an increasing interest in determining whether such proteins are present in tumor cells. These MBPs, generally homologs of the bacterial protein MutS, are referred to as MutS homologs (MSH) and are key elements of the mismatch repair system. Individuals heterozygous for a mutation in the human MutS homolog, hMSH2, are predisposed to a form of colon cancer (hereditary non-polyposis colon cancer or HNPCC) (Leach, S. S. et al., *Cell* 75:1212–1225 (1993); Fishel, R. et al., *Cell* 75:1027–1029 (1993)). Although the somatic cells of these individuals have normal levels of mismatch repair, HNPCC tumors have been found to be deficient in mismatch repair and have lost function of the homologous copy of the hMSH2 gene, generally by a second mutation Parsons, R. et al., *Cell* 75:1227–1236 (1993)). HNPCC tumors were originally characterized by the presence of microsatellite instability, also known as the replication error or "RER" phenotype. However, all RER tumors are not necessarily hMSH2 deficient. Mutations in other mismatch repair genes, in particular homologs of the bacterial mutL gene (mlh and pms), can also produce an RER phenotype (Papadopoulos, N. et al., *Science* 263:1625–1629 (1994); Bronner, E. C. et al., *Nature* 368:258–261 (1994)). Defects in other cellular functions may also give an RER phenotype (Bhattacharya, N. P. et al., *Proc. Natl. Acad. Sci. USA* 91:6319–6323 (1994)).

Current methods for determining if a tumor cell line is deficient in mismatch binding activity include in vitro mismatch repair assays and sequencing. Mismatch repair assays are somewhat laborious and cannot distinguish MSH deficiencies from MLH deficiencies unless complementation assays are performed. Sequencing is extremely laborious because the homologous chromosome sequences must be separately cloned and sequenced to distinguish heterozygotes from homozygotes. In addition, neutral polymorphisms, i.e., sequence differences between the homologs which do not affect protein function, can make interpretation of sequencing results difficult.

In response to these deficiencies in the art, the present inventor provides a simple, rapid and inexpensive assay for activity of a MBP in a test sample which does not require the use of gels, sequencing or radioactivity. The assay is based upon the immobilized mismatch binding protein mutation detection assay.

4. Triplet Repeats

A growing number of diseases is known to be associated with the expansion of "triplet" or trinucleotide repeat sequences (Trottier, Y. et al., *Current Biology* 3:783–786 (1993); Bates, G. et al., *Bioessays* 16:277–284 (1994); Kawaguchi, Y. et al., *Nature Genetics* 8:221–227 (1994)). In each of these diseases, the size of the repeat block directly correlates with, and thereby "anticipates" the severity and age of the onset of the disease. Some diseases are correlated with small increases in the size of the repeat block, for example, Huntington's disease. spino-cerebellar ataxia type I, spinal and bulbar muscular atrophy, Machado-Joseph disease and dentatorubralpallidoluysian atrophy. Other diseases involve up to 100-fold expansions of the normal block, such as fragile X type A, fragile X type E and myotonic dystrophy. In general, it appears that, if the repeated motif is short, for example, <10 nucleotides, and the repeat block is shorter than about 0.3 kb, replication slippage is the principal mechanism of instability (Kunkel, T. A., *Nature* 365:207–208 (1994)). If the repeat block is greater than 0.3 kb (the minimum size for efficient homologous DNA interactions), recombination and/or DNA methylation can affect the size and the sequence of such repeats.

"Satellite DNA" is a term used to describe highly repetitive sequences that are clustered together, and may consist of tandem repeats of a simple sequence. These range in size, with shorter sequences being termed "minisatellite" and yet shorter sequences described as "microsatellite." The most prevalent form of human microsatellite DNA comprises small expansions and contractions of $CA_n$ repeat blocks. These occur very frequently as a result of replication slippage in mismatch repair-deficient HNPCC tumor cells (Bronner, E. C. et al., *Nature* 368, 258–261 (1994)).

DNA methylation is found in the CGG repeats of fragile X syndrome (Trottier, Y. et al., *Current Biology* 3:783–786 (1993); Bates, G. et al., *Bioessays* 16:277–284 (1994); Radman, M. et al. In: *GENOME ANALYSIS*, vol 7 (Genome Rearrangement and Stability) eds. K. E. Davies et al., pp. 139–152 (1993)). Changes in "minisatellite" size (polymorphic repeat blocks several kb in length) and in DNA sequence occur by gene conversion (Jefferys, A. J. et al., *Nature Genetics* 6:136–145 (1994)). However, the mechanism of the rapid and large expansions of CGG/CCG and CAG/CTG repeats is unknown.

The present invention is designed in part to detect the presence of such expanded triplet repeat blocks for diagnosing diseases associated with such repeats.

SUMMARY OF THE INVENTION

The present inventor has conceived of the use of compositions and methods which employ immobilized mismatch binding proteins (MBPs), for example, the MutS protein of *E. coli*, for the following: (1) screening for or detection of genetic mutations, heterozygosity or genomic polymorphisms, (2) partial or complete purification of amplified DNA samples by removing contaminating sequences and sequences containing errors introduced during the amplification processes, and (3) identifying the presence of a specific allele in multi-allelic systems; (4) screening for the presence of either a specific known sequence in a selected region of an allele or an unknown sequence in the same selected region of a previously unknown allele of a multi-allelic system.

The nucleic acid, preferably DNA, being analyzed can be obtained from any source, including blood cells, tumor tissues, cells in culture or any tissue, and can be obtained from any species including humans. The DNA may be labeled by any of a variety of well-known methods, using calorimetric, chemiluminescent or radioactive markers. In fact, it is not necessary to label test DNA at all.

For detection of mutations or polymorphisms, the assay can be performed with a labeled competing oligonucleotide. For purification of amplified DNA, no label is required. For allele identification, the label must be in a synthesized single-stranded oligonucleotide probe.

The methods of the present invention depend on the creation of mismatches in the test DNA which are revealed by denaturing the test DNA and allowing it to reanneal. When testing for heterozygosity or for polymorphism within a test DNA sample, the test DNA can simply be self-annealed, resulting in formation of mismatches when the single strands reanneal with a strand descended from the other parental chromosome. If no heterozygosity exists, no mismatches will be formed. In this case, the label can be in the primers used for amplification or may be added to the termini of the test DNA if amplification is not required.

A similar procedure and labeling scheme is used to remove sequences containing errors introduced during amplification of DNA or minority sequence species. In these cases, the material which does not bind to the MBP is recovered, and contains only those duplex sequences without mismatches. These sequences will therefore be greatly enriched for the majority sequence in the amplified population. When the starting material contains only one sequence, the unbound material will contain those sequences which are identical to the starting material, while those sequences containing errors introduced during amplification will, provided they are relatively rare, have formed mismatches which are retained by the immobilized MBP. This method therefore allows purification of the faithfully replicated DNA or removal of a majority of error-containing sequences.

To detect homozygous mutations, it is necessary to anneal the test DNA in the presence of known wild-type sequences. Such sequences can be synthesized artificially or created during amplification by adding known wild-type sequences to the starting material before amplification. When annealing is performed in the presence of known wild-type sequences, the assay will detect both homozygous and heterozygous mutations.

For allele identification, it is necessary to add a labeled single-stranded probe DNA to the test DNA after amplification. The probe sequence must be identical to the allele of interest such that no mismatches are formed when it anneals to DNA of that allele. The sequence of the probe is selected so that it forms mismatches when annealed to the DNA of any other allele. When test DNA is annealed to such a probe (with the test DNA in excess such that the probe sequences all anneal to form a duplex) and exposed to excess immobilized MBP, the presence of unbound label indicates that the allele in question is present in the test DNA sample.

Thus, the present invention is directed to a method for detecting a mutation in heterozygous form in a test polynucleotide sample, preferably DNA, wherein the heterozygosity or mutation is the result of (i) a nucleotide substitution or (ii) a deletion or addition of up to about 4 nucleotides, which method comprises:

(a) obtaining test polynucleotide comprising sequences corresponding to all four DNA strands from a pair of chromosomes, or from a segment thereof, of a diploid organism;

(b) detectably labeling the test polynucleotide any time prior to step (c) below, and, optionally amplifying the test polynucleotide;

(c) denaturing any double stranded polynucleotide in the sample into single strands and allowing the single strands to reanneal into duplexes;

(d) incubating the detectably labeled polynucleotide duplexes with an immobilized mismatch-binding protein under conditions in which heteroduplexes containing a mismatch or one to about four unpaired bases bind to the immobilized protein; and (e) detecting the binding of any of the heteroduplexes of step (d) to the protein, wherein the presence of detectably labeled polynucleotide bound to the protein is indicative of the presence of the mutation in the test polynucleotide.

In the above method, the mismatch-binding protein is preferably *E. coli* MutS protein, or a homologue thereof from a different prokaryotic or eukaryotic species.

This invention further provides a method for detecting or screening for a homozygous or heterozygous mutation in a test polynucleotide, preferably DNA, in a sample, wherein the mutation is the result of (i) a nucleotide substitution or (ii) a deletion or addition of up to about 4 nucleotides, which method comprises:

(a) detectably labeling anytime prior to step (c) below,
  (i) the test polynucleotide, or
  (ii) an added polynucleotide or oligonucleotide, preferably DNA, as recited in step (b), below, or
  (iii) both (i) and (ii);

(b) denaturing double stranded polynucleotide in the sample into single strands in the presence of an added polynucleotide or oligonucleotide molecule having the wild-type sequence for the mutation, and allowing the strands to reanneal into duplexes;

(c) incubating the detectably labeled polynucleotide duplexes with an immobilized mismatch-binding protein under conditions in which heteroduplexes containing a mismatch or one to four unpaired bases bind to the immobilized protein; and (d) detecting the binding of any mismatch-containing double stranded polynucleotide from the sample to the protein, wherein the presence of detectably labeled polynucleotide or oligonucleotide bound to the immobilized protein is indicative of the presence of the mutation in the test polynucleotide.

In the above method, the sample polynucleotide may be amplified prior to step (b). The added polynucleotide or oligonucleotide of step (b) may be added prior to the amplifying step.

The present invention is also directed to a competitive assay method for detecting or screening for heterozygosity or the presence of a mutation in heterozygous form in test DNA in a sample, wherein the heterozygosity or the mutation is the result of (i) a nucleotide substitution or (ii) a deletion or addition of up to about four nucleotides, which method comprises:

(a) obtaining test DNA comprising sequences of all four DNA strands from a pair of chromosomes, or a segment thereof, of a diploid organism;

(b) denaturing double stranded DNA in the sample into single strands and allowing the single strands to reanneal into duplexes;

(c) incubating the denatured and reannealed duplexes of step (b) with a *E. coli* MutS protein, or a homologue thereof from a different prokaryotic or eukaryotic species, immobilized on a solid support, either
  (i) in the presence of a detectably labeled mismatch-containing oligonucleotide capable of binding to the protein; or
  (ii) wherein the immobilized protein was preincubated with and allowed to bind a detectably labeled mismatch-containing oligonucleotide,
  under conditions in which heteroduplexes containing a mismatch or one to four unpaired bases bind to the immobilized protein; and (d) detecting the amount of detectably labeled mismatch-containing oligonucleotide bound to the protein, wherein the presence of the heterozygosity or the mutation in the test DNA results in a decrease in the binding of the detectably labeled oligonucleotide to the protein.

In the method above, the sample DNA may be amplified prior to step (a).

Also provided is a competitive assay method for detecting or screening for a homozygous or heterozygous mutation in test DNA in a sample, wherein the mutation is either the result of a nucleotide substitution or a deletion or addition of up to about four nucleotides, which method comprises:

(a) denaturing any double stranded DNA in the sample into single strands in the presence of an added polynucleotide or oligonucleotide molecule having the wild-type sequence for the mutation, and allowing the single strands to reanneal into duplexes;

(b) incubating the denatured and reannealed duplexes formed in step (a) with a *E. coli* MutS protein, or a homologue thereof from a different prokaryotic or eukaryotic species, immobilized on a solid support, either
  (i) in the presence of a detectably labeled mismatch-containing oligonucleotide capable of binding to the protein; or
  (ii) wherein the immobilized protein had first been preincubated with, and allowed to bind to, a detectably labeled mismatch-containing oligonucleotide prior to the incubating, under conditions in which heteroduplexes containing a mismatch or one to four unpaired bases bind to the immobilized protein; and (c) detecting the detectably labeled mismatch-containing oligonucleotide bound to the protein, wherein the presence of the homozygous or heterozygous mutation in the test DNA of the sample decreases the amount of detectably labeled oligonucleotide bound to the protein.

In the method above, the sample DNA may be amplified prior to step (a). The added polynucleotide or oligonucleotide of step (a) may be added prior to the amplifying step.

In another embodiment, the invention is directed to a method for the removal from an amplified DNA sample of a majority of (i) sequences containing sequence errors introduced during the process of amplification and (ii) minority sequences, wherein the sequence errors and the minority sequences are the result of a nucleotide substitution or a deletion or addition of up to about 4 nucleotides, which method comprises:

(a) subjecting the amplified DNA sample to conditions of denaturation followed by reannealing, such that the error-containing or the minority sequences form heteroduplexes containing a mismatch or one to four unpaired bases, thereby generating a mixture of perfectly matched duplexes and the heteroduplexes;

(b) incubating the mixture of step (a) with an immobilized mismatch binding protein under conditions in which the heteroduplexes formed in step (a) bind to the immobilized protein; and (c) removing the immobilized protein to which the heteroduplexes are bound from the amplified DNA sample, thereby removing the majority of the sequences containing sequence errors and minority sequences from the amplified DNA sample.

Also provided is a method for screening a test DNA sample for the presence of either a specific known sequence in a selected region of an allele or an unknown sequence in the same selected region of a previously unknown allele of a multi-allelic system, wherein the known sequence is characterized as differing from other known sequences in the same selected region of other known alleles of said multi-allelic system by a nucleotide substitution or a deletion or addition of up to 4 nucleotides, which method comprises:

(a) mixing a detectably labeled oligonucleotide DNA probe, which probe
  (i) is perfectly complementary to the known sequence of the allele, and
  (ii) forms detectable heteroduplexes containing a single base mismatch or one to four unpaired bases when annealed with any other known sequences in the selected region of other known alleles of the multi-allelic system,
with an excess of the test DNA under conditions of denaturation followed by annealing such that, every copy of the probe is in a DNA homoduplex or heteroduplex;

(b) incubating the mixture formed in step (a) with an excess of immobilized mismatch binding protein under conditions in which the heteroduplexes formed in step (a) bind to the immobilized protein; and (c) removing the immobilized protein to which said heteroduplexes are bound from said test DNA; and (d) detecting the presence of said detectable label in the remaining mixture of step (c) from which the bound heteroduplexes have been removed, wherein, the presence of the labeled probe in the remaining mixture of step (d) indicates the presence in the test DNA sample of either
  (i) the said specific sequence, or
  (ii) the unknown sequence, which unknown sequence is characterized in that it differs from the known sequence such that when the unknown sequence is annealed to the probe, the resulting heteroduplex is not bound by the immobilized protein.

In the method above, the test DNA may be amplified DNA.

Also provided herein is a method for screening a test DNA sample for the presence of a mutation or polymorphism in a specific region compared to DNA of known sequence, wherein the mutation or polymorphism:
  (i) results from a nucleotide substitution or a deletion or addition of up to four nucleotides, and
  (ii) results in formation of a heteroduplex when a mutant or polymorphic DNA strand is paired with a DNA strand of known sequence, which heteroduplex is bound by a mismatch-binding protein,
the method comprising:

(a) detectably labeling the test DNA any time prior to step (c) below;

(b) denaturing double stranded DNA in the sample into single strands and allowing the single strands to reanneal into duplexes;

(c) incubating the detectably labeled DNA duplexes with an immobilized mismatch-binding protein under conditions in which heteroduplexes containing a mismatch or one to four unpaired bases bind to the immobilized mismatch-binding protein; and (d) detecting the binding of any of the heteroduplexes of step (c) to the immobilized protein, wherein the presence of detectably labeled DNA bound to the protein is indicative of the presence of the mutation or polymorphism in the known region of the test DNA.

The test DNA above may be amplified prior to step (b).

Also provided is a method for screening a test DNA sample for a homozygous or heterozygous mutation in a specific region of known sequence, wherein the specific mutation (i) results from a nucleotide substitution or a deletion or addition of up to about four nucleotides, and (ii) results in formation of a heteroduplex when a mutant DNA strand is paired with a DNA strand having the wild type sequence, which heteroduplex is bound by a mismatch-binding protein, the method comprising:

(a) detectably labeling anytime prior to step (c) below, the test DNA or an added DNA polynucleotide or oligonucleotide as recited in step (b), below, or both of the test DNA and the added DNA;

(b) denaturing any double stranded DNA in the sample into single strands in the presence of an added DNA polynucleotide or oligonucleotide molecule having the wild-type sequence for the mutation, and allowing the single strands to reanneal into duplexes;

(c) incubating the detectably labeled DNA duplexes with an immobilized mismatch-binding protein under conditions in which heteroduplexes containing a mismatch or one to four unpaired bases bind to the immobilized mismatch-binding protein; and (d) detecting the binding of any of the heteroduplexes of step (c) to the immobilized protein, wherein the presence of detectably labeled DNA bound to the protein is indicative of the presence of the mutation in the specific region in the test DNA.

In the method above, the test DNA may be amplified prior to step (b).

In another embodiment, the invention provides a method for detecting in a test DNA a heterozygous mutation in a specific region having a known sequence, wherein the mutation is the result of (i) a nucleotide substitution or (ii) a deletion or addition of up to about 4 nucleotides, which method comprises:
 (a) digesting the test DNA with one or two restriction enzymes to create a restriction fragment containing the site of the mutation, and, for PCR or other DNA synthetic amplification, preferably at least one primer site for initiation of DNA synthesis;
 (b) denaturing the restriction fragment into single strands and allowing the strands to reanneal into duplexes;
 (c) incubating the duplexes with an immobilized mismatch-binding protein under conditions in which heteroduplexes among the duplexes containing a mismatch or one to four unpaired bases bind to the immobilized protein;
 (d) removing any DNA not bound to the immobilized protein;
 (e) amplifying the DNA which contains the site of the mutation and which remains bound to the immobilized protein; and
 (f) detecting the amplified DNA,
wherein the presence of the amplified DNA is indicative of the presence of a mismatch in the annealed duplexes, thereby detecting the heterozygous mutation in the test DNA.

Also provided is a method for detecting a homozygous or heterozygous mutation having a known sequence in a specific region of a test DNA, wherein the mutation is the result of (i) a nucleotide substitution or (ii) a deletion or addition of up to about 4 nucleotides, which method comprises:
 (a) digesting the test DNA with one or two restriction enzymes to create a restriction fragment containing the site of the mutation, and, for PCR or other DNA synthetic amplification, preferably at least one primer site for initiation of DNA synthesis;
 (b) denaturing the restriction fragment into single strands in the presence of an added DNA polynucleotide or oligonucleotide molecule having the wild-type sequence for the mutation, and allowing the strands to anneal into duplexes;
 (c) incubating the duplexes with an immobilized mismatch-binding protein under conditions in which heteroduplexes among the duplexes containing a mismatch or one to four unpaired bases bind to the immobilized protein;
 (d) removing any DNA not bound to the immobilized protein;
 (e) amplifying the DNA which contains the site of the mutation and which remains bound to the immobilized protein; and
 (f) detecting the amplified DNA,
wherein the presence of the amplified DNA is indicative of the presence of a mismatch in the annealed duplexes, thereby detecting the homozygous or heterozygous mutation in the test DNA.

Another method of the present invention is directed to determining the presence or absence of a functional mismatch-binding protein in a biological fluid sample, comprising:
 (a) mixing the biological fluid sample with a detectably labeled double-stranded oligonucleotide heteroduplex containing a mismatch or mispairing, or a denatured single stranded oligonucleotide which will anneal to create the heteroduplex, thereby forming a mixture;
 (b) contacting the mixture with an immobilized mismatch-binding protein under conditions where the immobilized mismatch-binding protein binds to labeled heteroduplex in the mixture;
 (c) detecting the binding of any of the heteroduplexes to the immobilized protein,
 (d) separately detecting the binding of the labeled oligonucleotide heteroduplex to the immobilized protein in the absence of the sample,
wherein a decrease in the binding detected in step (c) compared to step (d) is indicative of the presence of a functional mismatch-binding protein in the sample.

A method for detecting the presence of a triplet repeat block of unit sequence

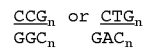

in a test DNA molecule in a sample, which block is longer than a triplet repeat block in a diagnostic oligonucleotide probe, which method comprises:
 (a) incubating the test DNA with a detectably labeled single stranded diagnostic oligonucleotide probe having a unit triplet repeat sequence $CGG_m$ or $CTG_m$, wherein
  i. n is the number of repeats of the triplet repeat block of the test DNA
  ii. m is the number of repeats of the triplet repeat block of the probe, and
  iii. n and m are integers,
 this probe preferably also including sequences of the DNA region flanking the triplet repeat sequences;
 (b) denaturing any double stranded DNA in the mixture of step (a) into single strands and allowing the strands to reanneal into duplexes;
 (c) incubating the mixture of step (b) with an immobilized mismatch binding protein under conditions in which heteroduplexes containing a mismatch or one to four unpaired bases bind to the immobilized protein; and
 (d) detecting the binding of any of the heteroduplexes of step (d) to the immobilized protein,
wherein the presence of detectably labeled DNA bound to the protein is indicative of the presence in the test DNA a triplet repeat block with a repeat number n greater than m.

In a related embodiment is provided a method for detecting the presence of a triplet repeat block of unit sequence

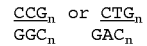

in a test DNA molecule in a sample, which block is shorter than a triplet repeat block in a diagnostic oligonucleotide probe, which method comprises:
 (a) incubating the test DNA with a detectably labeled single stranded diagnostic oligonucleotide probe having a unit triplet repeat sequence CGGm or CTGm, wherein
  i. n is the number of repeats of the triplet repeat block of the test DNA,
  ii. m is the number of repeats of the triplet, repeat block of the probe, and
  iii. n and m are integers, this probe preferably also including sequences of the DNA region flanking the triplet repeat sequences;

(b) denaturing any double stranded DNA in the mixture of step (a) into single strands and allowing the strands to reanneal into duplexes;

(c) incubating the mixture of step (b) with an immobilized mismatch binding protein under conditions in which heteroduplexes containing a mismatch or one to four unpaired bases bind to the immobilized protein; and (d) detecting the binding of any of the heteroduplexes of step (d) to the immobilized protein, wherein the presence of detectably labeled DNA bound to the protein is indicative of the presence in the test DNA a triplet repeat block with a repeat number n less than m.

The above method may be conducted with the following modifications: (i) prior to step (a), the test DNA is amplified to produce multiple copies of amplified oligonucleotides having the triplet repeat block sequence; and (ii) the amplified nucleotides are incubated in step (b) with the detectably labeled single stranded oligonucleotide probe.

In another embodiment, the invention provides a competitive assay method for detecting the presence of a triplet repeat block of unit sequence

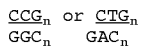

a test DNA molecule in a sample, which block is longer than a triplet repeat block in a diagnostic oligonucleotide probe, which method comprises:

(a) incubating the test DNA with a single stranded diagnostic oligonucleotide probe having a unit triplet repeat sequence $CGG_m$ or $CTG_m$, wherein
 i. n is the number of repeats of the triplet repeat block of the test DNA
 ii. m is the number of repeats of the triplet repeat block of the probe, and
 iii. n and m are integers;

(b) incubating the duplexes formed in step (a) with E. coli MutS protein, or a homologue thereof from a different prokaryotic or eukaryotic species, immobilized on a solid support, either
 i. in the presence of a detectably labeled mismatch-containing double stranded oligonucleotide capable of binding to the protein; or
 ii. wherein the protein was preincubated with and allowed to bind to a detectably labeled mismatch-containing double stranded oligonucleotide, under conditions in which heteroduplexes containing a mismatch or one to four unpaired bases bind to the immobilized protein; and (c) detecting the amount of detectably labeled mismatch-containing oligonucleotide bound to the immobilized protein, wherein a decrease in the binding of the detectably labeled oligonucleotide to the protein is indicative of the presence in the test DNA of a triplet repeat block with a repeat number n greater than m.

Another related competitive assay method detects the presence of a triplet repeat block of unit sequence

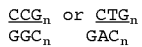

in a test DNA molecule in a sample, which block is shorter than a triplet repeat block in a diagnostic oligonucleotide probe, which method comprises:

(a) incubating the test DNA with a single stranded diagnostic oligonucleotide probe having a unit triplet repeat sequence $CGG_m$ or $CTG_m$, wherein
 i. n is the number of repeats of the triplet repeat block of the test DNA
 ii. m is the number of repeats of the triplet repeat block of the probe, and
 iii. n and m are integers;

(b) incubating the duplexes formed in step (a) with E. coli MutS protein, or a homologue thereof from a different prokaryotic or eukaryotic species, immobilized on a solid support, either
 i. in the presence of a detectably labeled mismatch-containing double stranded oligonucleotide capable of binding to the protein; or
 ii. wherein the protein was preincubated with and allowed to bind to a detectably labeled mismatch-containing double stranded oligonucleotide,
 under conditions in which heteroduplexes containing a mismatch or one to four unpaired bases bind to the immobilized protein; and (c) detecting the amount of detectably labeled mismatch-containing oligonucleotide bound to the immobilized protein, wherein a decrease in the binding of the detectably labeled oligonucleotide to the protein is indicative of the presence in the test DNA of a triplet repeat block with a repeat number n less than m.

The present invention provides methods of detecting an allele in a subject which, when passed to progeny, will result in a disease or syndrome associated with triplet repeats, including fragile X syndrome (type A or type E), myotonic dystrophy, Huntington's disease. spino-cerebellar ataxia type I, spinal bulbar muscular atrophy, Machado-Joseph disease and dentatorubralpallidoluysian atrophy.

In all the methods described above, the solid support is preferably selected from the group consisting of natural cellulose, modified cellulose, nitrocellulose, polystyrene, polypropylene, polyethylene, dextran, nylon, polyacrylamide, polyvinylidene difluoride, agarose and magnetic beads. A most preferred solid support is a nitrocellulose membrane.

The detectable label in the above methods is preferably a calorimetric compound, a chemiluminescent compound, a bioluminescent compound, a fluorescent compound or a radiolabel. Most preferably, the detectable label is biotin, detected by enzyme conjugated streptavidin.

In all of the methods of the present invention which utilize an MBP, the MBP is preferably E. coli MutS protein, or a homologue thereof from a different prokaryotic or eukaryotic species.

In another embodiment, the present invention is directed to kits useful for carrying out the methods described above. Provided is a kit useful for detecting a mutation from a non-mutated sequence of a target polynucleotide sequence in a sample, the kit being adapted to receive therein one or more containers, the kit comprising:

(a) a first container containing an immobilizable mismatch-binding protein;

(b) a second container containing a solid support capable of immobilizing the mismatch binding protein; and (c) a third container or a plurality of containers containing a reagent or reagents capable of detecting the binding of a detectably labeled mismatch-containing nucleic acid duplex to the mismatch-binding protein.

In another embodiment, the invention provides a kit useful for detecting a mutation from a non-mutated sequence of a target polynucleotide sequence in a sample, the kit being adapted to receive therein one or more containers, the kit comprising:

(a) a first container containing a mismatch-binding protein immobilized on a solid support;

(b) a second container or a plurality of containers containing a reagent or reagents capable of detecting the binding of a detectably labeled mismatch-containing nucleic acid duplex to the protein.

In the above kits, the mismatch-binding protein is preferably E. coli MutS protein, or a homologue thereof from a different prokaryotic or eukaryotic species.

In the above kits, the solid support is selected from the group consisting of natural cellulose, modified cellulose, polystyrene, polypropylene, polyethylene, dextran, nylon, polyacrylamide, polyvinylidene difluoride, agarose and magnetic beads. A most preferred solid support is a nitrocellulose membrane.

The present invention is further directed to a composition useful for detecting the presence of a mismatch or mispairing in a test polynucleotide or oligonucleotide heteroduplex, comprising a mismatch-binding protein immobilized on a solid support or matrix. The mismatch-binding protein is preferably E. coli MutS protein, or a homologue thereof from a different prokaryotic or eukaryotic species. The solid support is preferably selected from the group consisting of natural cellulose, nitrocellulose or other modified cellulose, polystyrene, polypropylene, polyethylene, dextran, nylon, polyacrylamide, polyvinylidene difluoride, agarose and magnetic beads.

BRIEF DESCRIPTION OF THE DRAWINGS

FIG. 12A and FIG. 12B depict schematically an exemplary probe to detect triplet repeat blocks DNA and the relationship between probe length, repeat block length in test DNA and detectability by immobilized MBP.

DESCRIPTION OF THE PREFERRED EMBODIMENTS

Figure 1:
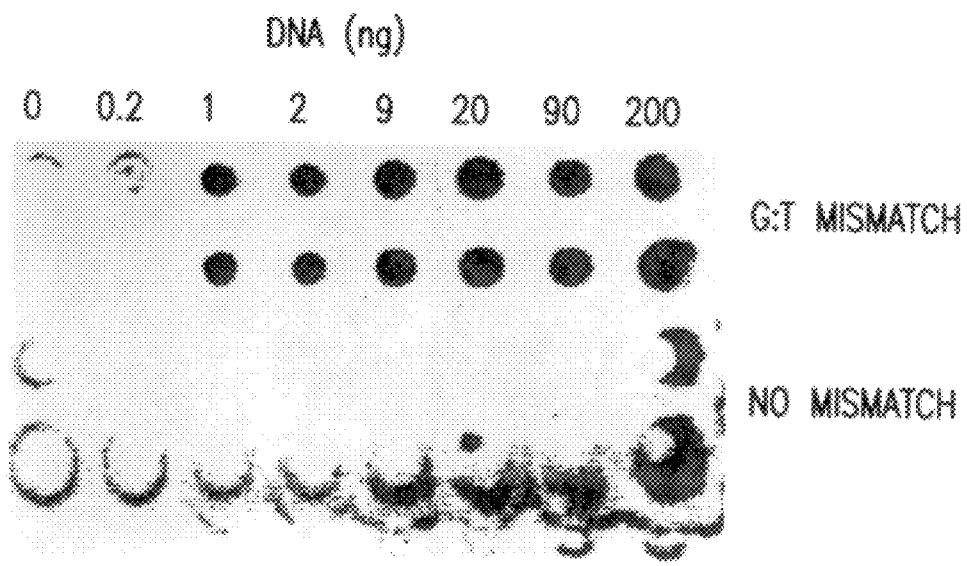
FIG. 1 shows the results of a direct assay of mismatches using nitrocellulose-bound MutS. Increasing amounts of biotinylated mismatch-containing DNA (upper 2 lines) or mismatch-free DNA (lower 2 lines) were added to the reaction mixtures.

The present inventor conceived of a new, broadly applicable and relatively simple method for detecting a single base change in a DNA sequence or several such base changes. This method is based upon the formation of a mismatch-containing heteroduplex when a strand of mutant DNA and a "complementary" strand of wild-type DNA hybridize.

The presence of the mismatch is detected in a highly specific manner by first allowing the DNA to bind to an immobilized mismatch-binding protein (MBP), such as the MutS protein of E. coli. The presence of DNA bound to the MBP is then detected in any of a number of ways, depending on the label used and whether the assay is a direct assay or a competitive assay. This method stands in stark contrast to methods of the prior art which employ mismatch cutting nuclease enzymes capable of breaking DNA at or near a mispaired base pair. The present method provides an increase in sensitivity of anywhere from greater than 5-fold to usually approaching 1000-fold in detection of those mismatches and mispairings detected by the same MBP in solution. A major advantage of the present assay lies in the fact that immobilized MBP (as shown with E. coli MutS) binds little or no homoduplex DNA even at relative high concentrations, in comparison with binding of homoduplex by MutS in solution, thereby allowing the powerful discriminatory ability of this assay.

The methods described herein provide a mutation/polymorphism detection system having the advantages of (a) simplicity, (b) accuracy, (c) ability to be used without radioactivity, (d) ability to detect all single base substitution mutations and addition or deletion mutations of 1–4 bases. The present invention also provides a method for detecting a functional MBP, or a deficiency thereof, in a sample, which is useful for screening normal or tumor cells for mismatch repair deficiencies. Such assays are important in the diagnosis of susceptibility to certain types of cancer.

Standard reference works setting forth the general principles of recombinant DNA technology and cell biology, and describing conditions for isolation and handling of nucleic acids, denaturing and annealing nucleic acids, hybridization assays, and the like, include: Sambrook, J. et al., *MOLECULAR CLONING: A LABORATORY MANUAL,* 2nd Edition, Cold Spring Harbor Press, Cold Spring Harbor, N.Y., 1989; Albers, B. et al., *MOLECULAR BIOLOGY OF THE CELL,* 2nd Ed., Garland Publishing, Inc., New York, N.Y., 1989; Watson, J. D., et al., *MOLECULAR BIOLOGY OF THE GENE,* Volumes I and II, Benjamin/Cummings Publishing Co., Inc., Menlo Park, Calif., 1987; Darnell, J. E. et al., *MOLECULAR CELL BIOLOGY,* Scientific American Books, Inc., New York, N.Y., 1986; Lewin, B. M., *GENES II,* John Wiley & Sons, New York, N.Y., 1985, which references are hereby incorporated by reference in their entirety.

MBPs are proteins of around 100 kDa, have been identified in and isolated from both bacteria and higher organisms and selectively bind DNA containing mismatched bases. MBPs have been found in yeast (Valle G et al., 1991 *Yeast* 7:981–988; Miret J. J. et al., 1993, *J. Biol Chem.* 268:3507–3513), as well as in humans (Stephenson, C. et al., 1989, *J. Biol. Chem.* 264:21177–21782; Karran, P et al., 1990, *Mutat. Res.* 236:269–275; Hughes M. J. et al., 1992, *J. Biol. Chem.* 267:23876–23882; Reenan, A. G. et al., 1993, *Genetics* 132:963–973; Reenan, A. G. et al., 1993, *Genetics* 132:975–985). Mismatch binding proteins from Xenopus and from mouse have been cloned by M. Radman and colleagues (Varlet et al., *Nucl. Acid Res.* 22:5723–5757 (1994)).

A preferred MBP is characterized by its ability to bind DNA—DNA (or DNA-RNA or RNA—RNA) duplexes containing mispaired or unpaired bases, to the significant exclusion of single stranded polynucleotides or perfectly matched duplexes. MBP binding to DNA duplexes is exemplified below. However, the fact that uridine is present in RNA while thymidine is absent does not preclude detection of RNA:DNA or RNA:RNA duplexes. RNA:DNA duplexes contain thymidine in the DNA strand and are expected to be bound by the MBP. An RNA:DNA mismatch-containing duplex could include a detectable G//T mispairing, which is among those most readily detectable by the present methods. *E. coli* MutS (in solution) is known to detect G//T, G//G and A//C mismatches (Wagner et al. PCT publication WO93/02216). Based on testing using nuclease protection, MutS is known to bind to all 8 possible mismatches in DNA (Su et al. (supra). All but thymidine-containing mismatches can occur and be detected in RNA:RNA duplexes. The only other chemical difference between DNA and RNA, the presence of the sugar deoxyribose vs. ribose in the sugar-phosphate backbone, is not known or expected to have any effect on binding of a mismatch-containing heteroduplex to MutS or any other MBP. Thus, while the preferred embodiments of the present invention are directed to detection of DNA—DNA duplexes, the methods disclosed herein are useful for detecting mismatches in any "polynucleotide" (or oligonucleotide) molecule, including RNA.

MISMATCH BINDING PROTEIN AND DERIVATIVES

In a preferred embodiment, the intact native MutS protein from *E. coli* is used. However, as used herein, the term "mismatch binding protein" or "MBP" is intended to encompass a functional derivative of the intact, native protein. By "functional derivative" is meant a "fragment," "variant," "analog," or "chemical derivative" of the protein which retains the ability to bind to a mismatch-containing nucleic acid heteroduplex, which permits its utility in accordance with the present invention.

A "fragment" of a MBP refers to any subset of the molecule, that is, a shorter peptide. A "variant" of the protein refers to a molecule substantially similar to either the entire protein or a DNA-hybrid-binding fragment thereof. A variant of a mismatch-binding protein, for example, of MutS, may be prepared by recombinant DNA methods well-known in the art.

A preferred functional derivative of MutS is a homologue of *E. coli* MutS in another species. The term homologue (or homolog) as used here in is well-defined in the art, and can be described as any member of a set of genes or DNA sequences from different organisms whose nucleotide sequences show a high degree of one-to-one correspondence (see, for example, Micklos, D. A. et al., *DNA SCIENCE,* Cold Spring Harbor Press, 1990, p. 468).

Examples of *E. coli* MutS homologues are the MutS protein of *Salmonella typhimurium* (Lu, A. L. et al., supra; Haber L. T. et al., supra; Pang, P. P. et al., supra) and the hexA protein of *Streptococcus pneumoniae* (Priebe S. D. et al., supra; Haber et al., supra). In addition, eukaryotic homologues of MutS or HexA can also be used, such as those encoded by the homologous sequences identified in yeast, human, mouse, frog or hamster DNA (Shimada, T. et al., *J. Biol. Chem.* 264:20171 (1989); Linton, J. et al., *Molec. Cell. Biol.* 7:3058–3072 (1989); Fujii, H. et al., *J. Biol. Chem.* 264:10057 (1989)).

The homology between MutS homologues in prokaryotic and eukaryotic species is illustrated in Reenan et al., *Genetics* 132:963–973 (1992), where the *E. coli* MutS nucleotide sequence is shown to be highly homologous in one region to *S. typhimurium* MutS, *S. pneumoniae* hexA, mouse Rep-1, and human DUC-1. PCR primers which successfully led to the cloning of *Saccharomyces cerevisiae* (yeast) homologues of MutS, named MSH1 and MSH2, were based on this homology. This reference shows the amino acid sequence homology between yeast MSH1, MSH2 and *E. coli, S. typhimurium* and *S. pneumoniae* MutS homologues. New et al., *Mol. Gen. Genet.* 239:97–108 (1993) disclosed another yeast gene, MSH3, which is a homologue of eukaryotic MutS and indicates the most conserved sequences among MutS, HexA and mouse REP-3. A search for a new yeast gene based on this sequence homology led to discovery of yeast MSH3. R. Fishel et al., *Cell* 75:1027–1029 (1993) describes the cloning of a another human MutS homologue (hMSH2) using for PCR the homologous sequences from other MutS homologues as described by Reenan et al., supra).

Therefore, any homologue of *E. coli* MutS which recognizes DNA mismatches (single base mismatches or 1–4 unpaired bases) is included within the scope of the present invention.

A "chemical derivative" of the MBP contains additional chemical moieties not normally a part of the protein, including additional stretches of amino acids as in a fusion protein. Covalent modifications of the peptide are included within the scope of this invention. Such modifications may be introduced into the molecule by reacting targeted amino acid residues of the protein with an organic derivatizing agent that is capable of reacting with selected side chains or terminal residues.

In selecting a protein as being a useful MBP for the methods of the present invention, assays can be performed by one of ordinary skill in the art using conventional methods of the prior art. However, novel methods described herein are preferred and are particularly well-suited for a simple screening method to detect a candidate MBP in a sample such as a cell extract. This method, described in more detail below, utilizes competitive binding of the unknown MBP to a known mismatch containing oligonucleotide to inhibit binding of a standard, known MBP such as *E. coli* MutS. Thus, in evaluating a candidate MBP, (or homologue or functional derivative) for utility in the present invention, a mismatch binding assay is performed using a known mismatch-containing heteroduplex. For screening cell extracts, or preferably, for evaluating the binding activity of a candidate MBP which has been identified, the cell extract or purified or semipurified candidate MBP is immobilized, as disclosed herein, and its binding to mismatch- or mispair-containing heteroduplexes is examined, for example, in an immobilized filter binding assay. To prepare the oligonucleotide heteroduplex, an oligonucleotide, preferably of about 30 bases, may be labeled with $^{32}P$ using a kinase reaction with $\gamma$-$^{32}P$-ATP and any appropriate kinase, for example, T4-polynucleotide kinase. Longer oligonucleotides may also be used. Alternatively, the oligonucleotide can be labeled with biotin at the 5'-end of one strand, as described below. The 5'-labeled oligonucleotide (which can be stored at −20° C.) is then annealed with a complementary oligonucleotide to form the desired mismatch under standard conditions. As described in more detail below for the competitive assay, the annealed heteroduplex is mixed with the preparation being tested for MBP activity and immobilized MutS. Alternatively, the labeled heteroduplex is mixed with the test MBP which has been immobilized as described herein. The heteroduplex is allowed to bind to the immobilized MutS or test MBP and label associated with the solid phase is determined. In the competitive assay, a decrease in bound heteroduplex compared to a control indicates the presence of an MBP recognizing the mismatch in the unknown. (In the direct assay, the presence of bound heteroduplex indicates that an MBP was bound to the solid phase.) Thus, by using such a simple assay, one can easily detect and select a MBP useful in the methods of the present invention.

As used in the detection, screening and "clean-up" methods of the present invention, the MBP is immobilized to a solid support or carrier. By "solid support" or "carrier" is intended any support capable of binding a protein while permitting washing without dissociating from the protein. Well-known supports or carriers include, but are not limited to, natural cellulose, modified cellulose such as nitrocellulose, polystyrene, polypropylene, polyethylene, polyvinylidene difluoride, dextran, nylon, polyacrylamide, and agarose or Sepharose®. Also useful are magnetic beads. The support material may have virtually any possible structural configuration so long as the immobilized MBP is capable of binding to the target nucleic acid molecule. Thus, the support configuration can include microparticles, beads, porous and impermeable strips and membranes, the interior surface of a reaction vessel such as test tubes and microtiter plates, and the like. Preferred supports include nitrocellulose disks or strips. Those skilled in the art will know many other suitable carriers for binding the MBP or will be able to ascertain these by routine experimentation.

Most preferred is a solid support to which the MBP is attached or fixed by covalent or noncovalent bonds. Preferably, noncovalent attachment is by adsorption using methods that provide for a suitably stable and strong attachment. The MBP is immobilized using methods well-known in the art appropriate to the particular solid support, providing that the ability of the MBP to bind mismatch-containing DNA is not destroyed.

The immobilized MBP is then easily used to detect heterozygosity (or polymorphism) as well as single base mutations and expanded trinucleotide repeats, or to isolate mismatch-containing DNA from a mixture, or to rid a mixture of mismatch-containing DNA.

In one embodiment, the surface of polystyrene or other plastic multiwell plates serves as the solid support. In another embodiment, a solid support to which the MBP is bound is affixed to the bottom or placed loosely in the wells of multiwell plates. Multiwell plates in which the bottoms of the wells comprise nitrocellulose or a similar membrane material and through which liquid can be moved under pressure or vacuum may also be used.

In a preferred embodiment, the immobilization and DNA binding can be performed in a 96- or 48-well blotting apparatus and the resulting sheet of nitrocellulose (or other support) paper can be removed to evaluate reactions. For example, color development on the nitrocellulose can be used to evaluate binding based on an enzyme as part of the detection system and a chromogenic or chemiluminescent substrate for the enzyme serving as the precursor of the color reactions.

Following attachment of the MBP to the support, the support is preferably treated ("blocked") to prevent further binding of proteins or nucleic acids, using methods and reagents well-known in the art.

The immobilized MBP is contacted with and allowed to bind (to saturation) small oligonucleotide heteroduplex molecules. The oligonucleotides preferably have about 30 base pairs. For testing, a DNA duplex containing a mismatch which is well recognized (i.e., bound) by the MBP is used.

PREPARATION OF OLIGONUCLEOTIDES CONTAINING OR LACKING MISMATCHES

Such oligonucleotides are prepared using a detectably labeled nucleotide, preferably modified at the 5' end with a detectable label, such that they can be quantitatively detected by appropriate detection methods, preferably spectrophotometry or chemiluminescence. As used herein, the term "detectable label" is intended to include not only a molecule or label which is "directly" detected (e.g., a radionuclide or a chromogen) but also a moiety such as biotin, which is "indirectly" detected by its binding to a second (or third) binding partner one of which carries the "direct" label. In a preferred embodiment, the oligonucleotide is biotin-modified, and is detectable using a detection system based on avidin or streptavidin which binds with high affinity to biotin. The avidin or streptavidin is preferably conjugated to an enzyme, the presence of which is detected by allowing the enzyme to react with a chromogenic substrate and measuring the color developed.

Non-limiting examples of useful enzymes in the methods of the present invention are horseradish peroxidase, alkaline phosphatase, glucose-6-phosphate dehydrogenase, malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase and acetylcholinesterase.

Other examples of detectable labels are: (1) a radioisotope which can be detected by such means as the use of a gamma counter or a scintillation counter or by autoradiography; (2) a fluorescent compound, which, when exposed to light of the proper wave length, becomes detectable due to it fluorescence and is measured by microscopy or fluorometry. Commonly used fluorescent labelling compounds include fluorescein isothiocyanate, rhodamine, phycoerythrin, phycocyanin, allophycocyanin, o-phthaldehyde and fluorescamine. The detectable label may be a fluorescence emitting metal such as $^{152}$Eu, or others of the lanthanide series which can be attached to the oligonucleotide using metal chelating groups such as diethylenetriaminepentaacetic acid or ethylenediaminetetraacetic acid.

The detectable label may be a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound may be used to label the oligonucleotide and is detecting by measuring luminescence. In this case, a catalytic protein increases the efficiency of the chemiluminescence reaction. Examples of useful bioluminescent labeling compounds include luciferin, luciferase and aequorin.

Mismatch-containing DNA—DNA, DNA-RNA or RNA—RNA duplexes can be detected either directly or indirectly. For direct detection, the poly- or oligonucleotide duplex is detectably labeled using labels as discussed herein. For indirect detection, the assay utilizes competition of binding to the MBP of the test DNA with an already bound or a contemporaneously exposed mismatch-containing oligo- or polynucleotide duplex. Thus, for example, a labeled mismatch-containing DNA oligonucleotide is prebound to the MBP or is incubated together with the MBP and test DNA. The more mismatch-containing DNA in the test sample, the less binding of the labeled oligonucleotide to the MBP will occur.

The test sample to be assayed can be in any medium of interest, and will generally be a sample of medical, veterinary, environmental, nutritional, or industrial significance. Human and animal specimens and biological fluids particularly can be assayed by the present method, providing that they contain cells from which nucleic acids can be prepared. Preferred sources include blood, sperm, other tissue (particularly tumor tissue or cells), milk, urine, cerebrospinal fluid, sputum, fecal matter, lung aspirates, throat swabs, genital swabs and exudates, rectal swabs, and nasopharyngeal aspirates. Preferred biological fluids in which the presence or absence of a functional MBP may be determined according to this invention include cells and cell extracts or any body fluid as above, or a protein-containing fraction of such an extract or fluid.

A key advantage of the present invention stems from the use of an immobilized MBP, as compared to a soluble MBP, for detecting mismatch-containing DNA. This discovery by the present inventor did not flow naturally from the teachings in other related fields such as the immunoassay art. First, the fact that a complex "AB" of two components (A and B) formed in solution binds to a solid support Z to yield ABZ does not ensure that A will interact effectively with BZ or that B will interact effectively with AZ. The order in which A and B bind to form a complex may be significant. This is especially noteworthy in the case of MutS or other MBPs which function physiologically as part of a complex pathway of mismatch repair.

Therefore one must exercise caution in trying to analogize between the binding behavior of, for example, antibodies and an MBP. Antibodies and MutS differ fundamentally in the way in which they recognize varying structures. MutS recognition is particularly targeted to a minimal deviation from a normal base paired structure, while being non-existent for the normal base pair. In other words, almost counter-intuitively, the more a mismatch "looks like a match," the more likely it is to be recognized by MutS (Fazakerley et al., *EMBO J.* 5:3697–3703 (1986)). Thus, for example, MutS varies from (1) absolutely no recognition of a G:C match to (2) optimal recognition of the most minimal (as determined by nuclear magnetic resonance) mismatch G//T, to (3) poor recognition of a more distinct mismatch, C//C. An antibody optimally recognizes a particular antigenic structure or epitope; as the structure of the epitope is gradually modified, antibody binding falls off proportionally until the epitope structure is sufficiently distinct that no recognition is observed any longer. The "recognition pattern" of MutS for C//C, G//T and G:C would never have been predicted from knowledge of antibody-antigen recognition. For the foregoing reasons, results and conclusions drawn from the antibody art cannot be considered simply transferable to the binding of nucleic acids by MutS in the methods of the present invention.

Until the discovery by the present inventor, it was not predictable that MutS could be immobilized and still retain its DNA binding properties. As stated above, the order of binding of reactants is not trivial. Thus, the binding of a MBP (e.g., MutS) to DNA to yield a MutS-DNA complex, which then binds to nitrocellulose (NC) yielding MutS-DNA-NC, is not equivalent to the binding of MutS to NC to yield immobilized MutS-NC which then binds to DNA in solution to yield DNA-MutS-NC. It is also noteworthy that MutS does not interact in solution directly with the next protein in the physiological mismatch repair sequence, MutL; however, once MutS has bound DNA, the complex then binds to MutL (Grilley et al., *J. Biol. Chem.* 264:1000–1004 (1989)). This further supports the notion that order of binding is important in MutS interactions.

Further evidence that binding in solution of a DNA binding protein to DNA is not predictive of binding in immobilized form comes from studies performed by the present inventor showing that the DNA-binding protein recA from *E. coli* (which is not a mismatch binding protein) lost its ability to bind DNA after immobilization on nitrocellulose. This finding further supports the unexpected nature of the present invention.

DETECTION OF HETEROZYGOSITY OR POLYMORPHISM

A mutation never exists as a mismatched base pair once DNA has replicated following the original mutational event.

Rather, the mutated base will exist in the DNA in vivo in the form of a "matched" (albeit mutant) base pair. The existence of this mutation may be revealed as a mismatch using the methods disclosed herein. For such detection it is necessary to denature and anneal DNA to obtain a detectable mismatch.

The types of mutations that can be detected by the present methods include both homozygous and heterozygous mutations. Heterozygosity really means nothing other than the presence on one of a pair of homologous chromosomes of a DNA sequence difference. Depending upon the context, such a sequence difference is commonly referred to as a mutation ("heterozygous mutation") or as an alternative "allele" for a given genetic locus. By definition, heterozygosity only exists in DNA of a diploid organism.

However, the present methods are not limited to testing heterozygous or diploid organisms, because any detectable sequence difference among a population of DNA molecules in a sample (i.e., a difference that, under assay conditions, will produce a mismatched or mispaired heteroduplex bound by the MBP) can be screened for, or detected, using the present methods. In other words, the principle underlying the detection of homozygous mutations by the present methods is applicable to viral or bacterial DNA sequences or other non-diploid DNA species.

While it is important that the test DNA used in the present method comprises sequences of all four DNA strands from one or more pairs of chromosomes of a diploid organism, it is not necessary that DNA from the entire chromosome be included in the assay. That is, fragments of DNA much shorter than a chromosome can be tested for the presence of a heterozygous mutation using the present method as long as, for the region containing the mutation (or heterozygosity), nucleic acid sequences representing the sequence of both strands of both chromosomes is present in the assay.

It is also important to note that the present method does not require a double stranded DNA preparation be used to initiate the assay. Thus, for example, a conventional double stranded diploid test DNA preparation may be heated or otherwise denatured into single strands, maintained in this denatured state for a prolonged period and shipped in this single stranded form to a testing laboratory which utilizes the present methods. The testing laboratory then carries out the assays described herein using as its "test DNA" this single stranded (rather than a conventional double stranded) preparation. This assay is operable and will yield the same results as if the testing laboratory had used as its "test DNA" a conventional double stranded DNA preparation from cells of a diploid organism. This example illustrates that the present methods can be practiced successfully without a strict requirement for a double stranded DNA preparation in the assay itself; several embodiments of this invention provide the necessary second DNA strand for creation and detection of DNA mismatches and mispairings.

In the case of heterozygosity, the mismatch which is detected (and is created during the assay) occurs between two strands of DNA from the same individual (test DNA from the homologous chromosomes). However, the present methods are also capable of detecting "population heterozygosity," wherein a "variant" nucleotide sequence can exist at a level well below the 50% common for a heterozygous allele in a diploid cell. Thus, the present methods allow detection of such population heterozygosity in a population of eukaryotic somatic cells (preferably human), bacterial cells or viral particles where a difference recognizable by a MBP is present in only a small proportion of cells (or DNA molecules).

For detection of homozygous mutations, described below, the mismatch will occur in the pairing of the denatured DNA strands with a wild-type (or different) DNA strand added as part of the assay method. With the present methods, no a priori choice between these two possibilities must be made in selecting a test DNA to be analyzed. The methods described herein are operable with any DNA containing a mutation, either heterozygous or homozygous.

The method of the present invention is capable of detecting a mutation of the type described herein (or heterozygosity or polymorphism), even if one or several of the eight possible mismatches are not detectable. The present inventor as well as others have failed to detect C//C mismatches in a number of their experimental determinations because $E.\ coli$ MutS binds less well to C//C as compared to other mismatches. Note however, in Example II, below, the C//C mismatch could be detected using the present method. Yet even when binding to C//C is poorly detectable (or undetectable) in a given test on a given day or under a given condition, the present methods nevertheless enable detection of a mutation in which the DNA of one pair of strands produces a C//C mismatch during the assay. This is because the complementary pair of DNA strands will yield a G//G mismatch which gives a strong signal using the present method. Therefore, even if a given MBP, such as a MutS homologue from another bacterial species or from a eukaryotic species, does not bind detectably to all eight possible mismatches, this MBP can nevertheless detect all mutations when used according to the present methods.

To detect heterozygosity or polymorphism in DNA from a diploid organism, test DNA is preferably prepared by denaturing and annealing amplified DNA from a diploid organism. The test DNA is prepared with labeled primers, annealed and added to a well or other reaction vessel which contains immobilized MBP already bound to mismatched oligonucleotides. Alternatively, test DNA can be mixed with mismatched oligonucleotides and the mixture added to a well or other vessel containing immobilized MBP.

A spectrophotometric reading is made at the wavelength appropriate for quantitative detection of the test DNA. After an incubation period suitable to allow either (1) binding of the test DNA to the immobilized MBP or (2) displacement of the mismatched oligonucleotide from the immobilized MBP, the DNA solution is removed, the well washed, and a spectrophotometric reading made at the wavelength appropriate for quantitative detection of the bound mismatched oligonucleotide.

The ratio of the reading for test DNA to the reading for the mismatched oligonucleotide will be vastly different for mismatch-containing and mismatch-free test DNA over a wide range of DNA concentrations. Standard curves are prepared using known quantities of DNA to allow characterization of test DNA as homozygous or heterozygous without having to quantitate the test DNA prior to the assay. Thus, a single DNA sample is sufficient to determine heterozygosity and, for example, a single 96-well microplate will allow the testing of at least about 80 different DNA samples.

DETECTION OF HOMOZYGOUS MUTATIONS

To detect a homozygous mutation from wild-type, known wild-type DNA must be combined with the test DNA sample before, or at the time of, denaturing and annealing. Only test DNA containing a mutation (heterozygous or homozygous)

will form a mismatch-containing heteroduplex with this added wild-type DNA. Such a heteroduplex will compete, for example, with the detectable (e.g., biotin-labeled) mismatch-containing oligonucleotide for binding to immobilized MBP. One skilled in the art will appreciate that this method will detect equally well a "mutation" from mutant to wild-type (i.e., a reverse mutation). In fact, the "mutant" and "wild-type" nomenclature is simply a convention of convenience. The presence of two nucleotide sequences which result, following denaturation and re-annealing, in a mismatch or mispairing recognized by the immobilized MBP is detectable using the present methods.

The method of the present invention can be used with (a) only the mismatched oligonucleotide labeled or (b) only the test DNA labeled. When the mismatched oligonucleotides are labeled, the test is a competitive assay, based on competition of the labeled oligonucleotide heteroduplex with several different concentrations of test DNA. The competing oligonucleotide may either be mixed with the test DNA in solution or may be pre-bound to the MBP. The resulting curve (with concentration expressed as moles of duplex molecules) is compared with a standard curve obtained with a mismatched standard and a perfectly matched standard.

When the test DNA is labeled, the test preferably involves measuring the extent of binding to the MBP at several concentrations below saturation and comparison of the resulting curve with standard curves for a mismatched standard and a perfectly matched standard.

The test DNA which is examined for the presence of a mutation is preferably mammalian DNA, more preferably human DNA. However, the present methods may also be used with DNA obtained from any non-mammalian species, including both eukaryotic and prokaryotic DNA.

The present methods are particularly useful for screening for the absence of a mutation. If a nucleic acid sample tests negative in the present methods, it can be safely concluded that the sample contains no variant DNA which will form a mismatch with the wild-type sequence (or a known sequence which is added to the assay).

The present methods using immobilized MBP may also be used to screen for specific known mutations, although these methods must be followed by sequencing to verify the identity of the specific mutation. For such screening methods, the mutation must have a known sequence compared to the wild type sequence. Mutations detectable using the present methods are ones which result from a nucleotide substitution, a deletion or the addition of 1–4 nucleotides which produce heteroduplexes when the DNA is annealed with wild-type sequences. The mutations which may be screened are those which result, during the assay, in creation of mispaired heteroduplexes of the types recognized and bound by the MBP or functional derivative of the invention.

Thus, a preferred MBP (even if not strictly a MutS homologue as defined herein) for the present invention is one which recognizes the specific types of mispairings. A preferred MBP is characterized by its ability to bind duplexes containing mispaired or unpaired bases, to the significant exclusion of single stranded polynucleotides or perfectly matched duplexes (see above). Also included in the scope of the present invention are MBPs which recognize a different array of mismatches or mispairings than does *E. coli* MutS. As long as the nature of the mismatches or mispairings recognized by the protein are characterized, the protein can be used in the presently disclosed methods to detect mutations, heterozygosity and polymorphisms defined by the range of heteroduplex structures recognized by the MBP protein. One skilled in the art will readily appreciate which MBPs can be used to identify which types of mismatches or mispairings or unpaired bases in the methods disclosed herein without undue experimentation.

PURIFICATION OF AMPLIFIED DNA SAMPLES

One of the most revolutionary and widely used technologies currently employed in modern molecular biology is the process of polymerase chain reaction (PCR), which amplifies DNA sequences from starting amounts so minute as to be nearly undetectable. For reviews of PCR, see: Mullis, K. B., 1986, *Cold Spring Harbor Symp. Quant. Biol.* 51:263–273; Saiki, R. K. et al., 1985, *Bio/Technology* 3:1008–1012; and Mullis, K. B. et al., 1987, *Meth. Enzymol.* 155:335–350. In addition, because PCR can amplify specific sequences, it allows the purification of specific sequences, basically in a single step, from genomic DNA. PCR is an essential component of virtually all studies of the human genome, is a central component of gene identification and cloning, is increasingly used in the diagnosis of genetic and infectious diseases and is widely used in forensics.

However, for some applications, in particular, gene cloning and mutation detection, PCR suffers from an inherent tendency of the polymerases to make mistakes by inserting incorrect, non-complementary bases during synthesis. Although the fidelity of in vivo DNA replication, including mismatch repair, is such that only one incorrect base is inserted for every $10^{10}$ bases replicated, polymerases used in PCR can have error rates as high as one incorrect base for every $10^4$ bases replicated. This high an error rate can mean that a significant fraction of the amplified molecules will not be identical in sequence with the starting material.

The present methods include using an immobilized MBP to remove a major proportion of error-containing sequences and minority sequences from PCR amplified material, which results in relative (and possibly complete) purification of the amplified DNA. Those errors that are detected and removed are those which result from a nucleotide substitution, a nucleotide deletion or the addition of up to about 4 nucleotides. For example, if a DNA segment is amplified through 20 rounds of replication (a common amount of amplification), a significant fraction of the molecules generated may contain one or more incorrect bases. In cloning experiments, this greatly increases the risk of cloning a nucleotide sequence different from the starting sequence.

In mutation detection assays involving denaturation and annealing of a PCR-amplified sample, incorrect bases inserted during PCR may be scored as if they were mutations in the original sample. Thus, for accurate mutation detection it is necessary to eliminate all DNA molecules with sequence alterations introduced by PCR copy errors. The method described here accomplishes this purification in a simple and straightforward manner.

Immobilized MBP is used to purify amplified DNA samples. MBP is immobilized by binding to solid phase supports, preferably nitrocellulose filters, sepharose beads or magnetic beads. The filters or beads are treated, if necessary, to prevent the binding of double-stranded DNA. The amplified DNA sample is denatured, by heating, and allowed to reanneal. Given the random nature of PCR mistakes, virtually all incorrect bases will be found in mismatched base pairs after annealing.

The immobilized MBP is added to the sample and the solution mixed by gentle shaking. The immobilized MBP, and any bound mismatch-containing DNA, is removed, for example, by removing the filter, by centrifuging or allowing the beads to settle out of solution or by removing the beads magnetically, depending on the nature of the solid support used. In a preferred embodiment, the DNA solution is removed by vacuum filtration through solid phase filters such as nitrocellulose, to which the MBP is immobilized. The DNA duplexes left behind in solution are precisely matched duplexes.

In yet another embodiment of the present invention, amplified error-containing DNA may be removed from a PCR sample using soluble MBP. As above, the amplified DNA sample is denatured, by heating, and allowed to reanneal, leading to a state wherein incorrect bases are found in mismatched base pairs after annealing. This amplified reannealed material is mixed with an excess of about 5–100-fold of soluble MBP which is allowed to bind to mismatched heteroduplexes. The DNA-MBP complex is then allowed to adhere to a solid phase, such as a filter, preferably a nitrocellulose filter. Only mismatch-containing DNA bound to the MBP will bind to the filter. The now immobilized complex of MBP and mismatch-containing DNA is removed, for example, by removing the filter or by other means described above or well-known in the art. The DNA duplexes left behind in solution are precisely matched duplexes. This latter approach, while having lower apparent specificity than the method utilizing immobilized MBP, may offer advantages of greater capacity for bulk preparations.

In addition to purifying amplified DNA samples by removing molecules containing errors introduced during amplification, purification using an immobilized MBP is used to enrich for majority sequences during examination of samples of diverged, repeated DNA sequences, such as of immunoglobulin genes.

To remove completely a minority species from a DNA sample amplified from a mixed population of DNA (with respect to sequence), it may be necessary to perform more than one round of purification, as described herein, which may entail more than one round of amplification.

It is noteworthy that the present method can be used to purify sequences from both homozygous and heterozygous amplified sequences, since half of the parental sequences in a heterozygous sample will anneal to the complementary strand of the same parental heritage and thus form a molecule without mismatches. In other words, when the starting material is heterozygous DNA, half of the annealed molecules will be removed from the sample because they contain a mismatch due to differences in the starting sequences. However, half of the annealed molecules will not contain such mismatches and so will be removed from the sample only if they contain mismatches which were created as a result of errors during amplification. In any event, mutation detection assays will require a second round of denaturing and annealing.

While the present methods are particularly well-suited to remove error-containing sequences from PCR amplified DNA, the same methods can be used to remove sequences containing errors introduced during any type of DNA synthesis, such as normal DNA replication occurring in vivo. Because of the nature of the assay and of MBP recognition of mismatches/mispairings, any DNA containing an error leading to formation of a recognized mismatch can be removed. The DNA must not necessarily be "amplified" as the term is commonly used to describe DNA which has been subjected to PCR or similar amplification in vitro, or phage or plasmid DNA which can be considered to have been amplified in vivo.

ALLELE IDENTIFICATION IN MULTI-ALLELIC SYSTEMS

As more alleles of disease-causing genes are identified, and in the quest to develop a polymorphism map of the human genome, it is becoming increasingly important to be able to identify particular alleles of a given gene. Immobilized MBPs provide a simple and straightforward means of allele identification.

In principle, heterozygosity at a given locus wherein the two alleles differ by a single base pair (or small insertion or deletion) is no different than a "heterozygous mutation." The existence of two different alleles in the DNA of a single diploid subject can be detected by the claimed methods after denaturation and annealing, without the need of an additional wild-type polynucleotide strand. The methods disclosed herein can detect the presence of a sequence alteration (leading to a single base mismatch or mispairing in the assay, as above) which exists in the form of an allele or a variant for a genetic region that is polymorphic in a species (i.e., has more than one variant form) or, in other words, is part of a multi-allelic system. For detection by $E.$ $coli$ MutS or homologue thereof, the allele or polymorphic variant must differ from the wild-type sequence, or from any "known sequence" for that particular genetic region, by a single base substitution or an addition or deletion of up to four bases. If a different MBP with a different mispairing specificity than MutS is used, then a different range of sequence differences leading to mismatches/mispairings will be detectable, as would readily be appreciated by one skilled in the art.

The present methods permit screening a test DNA sample for the presence of a specific known sequence in a selected region of an allele, with the understanding that, in those rare instances when a previously unknown allele which has a yet unknown sequence in the same selected region is present, a false positive result could be obtained. The known sequence, above, is characterized as differing from other known sequences in the same selected region of other known alleles of this multi-allelic system by a nucleotide substitution or a deletion or addition of up to 4 nucleotides recognized by the MBP. The unknown sequence above which could give rise to a false positive result is characterized in that it differs from the known sequence such that when the unknown sequence is annealed to the probe (below), the resulting heteroduplex is not bound by the immobilized MBP used in the assay (i.e., lacks a detectable mismatch or mispairing).

In such a screening method, a detectably labeled oligonucleotide DNA probe is used. This probe is characterized in that it (i) is perfectly complementary to the known sequence of the selected region of the specific allele, and (ii) forms detectable heteroduplexes (containing a single base mismatch or one to four unpaired bases) when annealed with any other known sequences in the same selected region of other known alleles of this multi-allelic system.

Such a probe is mixed with excess test DNA, which preferably has been amplified, under conditions of denaturation followed by annealing such that, after denaturing and annealing, every copy of the probe is in a DNA homoduplex or heteroduplex. This duplex-containing mixture is then allowed to bind to an excess of immobilized MBP such as $E.$ $coli$ MutS protein under conditions in which heteroduplexes formed above bind to th immobilized protein. The immobilized protein to which these heteroduplexes are bound is removed from the test DNA. The presence of detectable (probe) label in the mixture from which heteroduplexes have been removed by the immobilized MBP indicates the presence in the test DNA of either (a) the specific known sequence in the selected region of the allele, or (b) the unknown sequence, both as characterized above.

As is evident from the foregoing, for allele identification (in contrast to heterozygous mutation detection), added probe sequences are required in the present methods. A unique, labeled oligonucleotide probe can be prepared for a selected region of each allele of a given gene, such that the probe is perfectly complementary to the region of only one allele and forms one or more detectable mismatches or mispairings when paired with any other allele. As above, the probe is mixed with an excess of (amplified) test DNA such that, after denaturing and annealing, every copy of the probe will be found in duplex. The process can then be repeated with probes representing every allele in the multiallelic system. Removal of heteroduplexes (mismatched DNA) from the mixture can be accomplished using any of a number of means, including:

(1) mixing the with immobilized MBP on a support that can be removed from the suspension by centrifugation;

(2) passing through a micro-column of immobilized MBP on an appropriate column support; or (3) passing through a filter support containing immobilized MBP.

In yet another embodiment utilizing a soluble MBP, the annealed DNA mixture as above is (4) mixed with soluble MBP, which is then allowed to bind to a solid phase support such as a nitrocellulose filter, as described above for removal of error containing DNA following PCR amplification.

As stated above in connection with purification of amplified DNA, this embodiment may provide enhanced capacity at the expense of lower specificity compared to the immobilized MBP method.

In the above allele-identification or screening methods, the immobilized MBP (or soluble MBP, as the case may be) must be in excess such that all mismatch-containing DNA is bound and retained. The supernatant, column flow through or filtrate is analyzed for the presence of label. Label will be detected only in those cases where the probe is perfectly complementary to the sequence of an allele represented in the test DNA.

In order to be certain that no single-stranded probe sequences are present, it may be necessary, or at least desirable, to include some single-stranded DNA binding component on the support for the immobilized MBP. This system works equally well for homozygous or heterozygous conditions.

DETECTION OF FUNCTIONAL MISMATCH BINDING PROTEINS IN CELL EXTRACTS OR PURIFIED PROTEIN PREPARATIONS

This method is based upon the immobilized mismatch binding protein mutation detection assay as described above. In particular, this assay is based upon the ability of an MBP in solution to interfere with the immobilized MBP assay.

The assay is generally performed as described below. A biological sample being tested for the presence of a functional MBP, preferably a cell or tissue extract or a protein-containing fraction from such an extract, is mixed with a double-stranded oligonucleotide containing a mismatch which is readily bound by an immobilized MBP. Thus, in a preferred embodiment, the immobilized MBP is E. coli MutS and the oligonucleotide contains a well-recognized single base pair mismatch, preferably G//T, (or one to four unpaired bases) any of which mismatches or mispairings is recognized by E. coli MutS. The oligonucleotide may be in the form of a mismatch-containing heteroduplex or denatured single strands which under assay conditions will anneal to form the mismatch-containing heteroduplex.

An example of such a heteroduplex (see Examples, below) is a synthetic 30 mer oligonucleotide with a G//T mismatch at position 15 and a 5' biotin label. Particularly when a cell extract is used, the method may require a mixture of (1) labeled mismatch-containing oligonucleotide and (2) an excess of unlabeled double-stranded DNA lacking mismatches which serves to bind any non-specific DNA binding proteins which may be present in the extract thereby minimizing their interference with the activity of specific MBP in the sample.

After an appropriate incubation, the mixture is contacted with an immobilized MBP, preferably E. coli MutS, as described in detail above. If the protein preparation or extract contains MBPs, the signal in the immobilized mismatch binding protein assay will be reduced. In other words, the MBPs in the sample will have bound to any labeled heteroduplex DNA, thus preventing such heteroduplex DNA from binding to the immobilized MBP.

To ensure that reduction in binding is due to the presence of an MBP in the sample and not to destruction of the of the labeled oligonucleotide probe by any nucleases in the sample, a separate aliquot of the above mixture is heated to inactivate MBPs, for example at 70° C. for 10 minutes, or under alternate conditions of time and temperature known to the skilled artisan. The immobilized mismatch binding assay is repeated on this heat-treated sample. If the absent or reduced mismatch binding signal is recovered, following such treatment, this result indicates that the activity detected was DNA binding activity and not an artifact of nuclease digestion of the oligonucleotide.

The assay preferably includes a control which comprises a known MSH2 deficient extract.

Using this method, a sample of cells from a subject suspected of being susceptible to a form of cancer associated with a deficiency in mismatch repair, for example hereditary non-polyposis colon cancer, can be tested in a simple and economic manner. This approach lends itself to an inexpensive screening procedure for large numbers of samples.

MISMATCH DETECTION BY AMPLIFICATION OF DNA BOUND TO IMMOBILIZED MISMATCH BINDING PROTEIN

The present invention is also directed to a method for detecting mismatches in which test DNA, preferably a sample of genomic DNA, is first subjected to digestion with restriction enzymes, denatured and reannealed and then allowed to bind to an immobilized MBP. If the sequence of interest containing the mutation is present, it becomes amplified "in situ".

This method depends upon prior knowledge of the sequence of interest so that appropriate restriction sites can be identified and an appropriate probe designed which will result in an MBP-detectable mismatch.

Test DNA, typically genomic DNA, with known sequence in a specific region, is subjected to restriction enzyme digestion such that the region of interest and a primer site or sites (for PCR or other DNA polymerase-based synthesis) are contained in a single restriction fragment. This digested DNA is then denatured and annealed, as described above. For a heterozygous mutation, the mismatch will be created upon reannealing with a DNA sequence from the homologous chromosome. For homozygous mutations, DNA having the wild-type sequence for the site of interest must be added prior to or during the annealing step.

The annealed DNA is then exposed to immobilized MBP, preferably MutS, and mismatch-containing heteroduplexes are allowed to bind. Unbound DNA is removed by washing. A primer or primers for DNA synthesis are added to the bound DNA and the DNA is amplified. Preferably, this is done using PCR. However, if the restriction fragment being tested is of sufficient size, a single round of DNA replication using, for example, E. coli DNA polymerase or T4 polymerase, may suffice to generate a detectable signal.

The product of the amplification may be detected by any of a number of methods. For example, for maximal simplicity, incorporation of a label such as a radiolabeled nucleotide into TCA precipitable DNA can be measured. Alternatively, detection may be accomplished using known gel electrophoresis methods to identify a characteristic oligonucleotide band. If there was no mutation in the test sample, there would be no incorporation of label into DNA because no DNA will have been bound to the MBP. Similarly, recovery of a PCR product is indicative of the presence of a mismatch in the annealed fragments, and therefore a mutation in the sample DNA. If no exogenous (probe) DNA was added to the assay, then a positive result indicates a heterozygous state of the test DNA. A positive result in the case where wild-type DNA had been added to the sample is indicative of a homozygous or heterozygous mutation in the sampled restriction fragment.

A two step assay may also be performed in which the first step is carried out without added wild-type DNA. A heterozygous mutation would yield a positive signal whereas either a homozygous mutation or no mutation would give a negative result. A second step is then carried out in which wild-type DNA is added. A positive signal here indicates a homozygous mutation whereas a negative result indicates the absence of any mutation.

It is noteworthy that any sequence based DNA amplification or synthesis method, including PCR and the ligase chain reaction method, will allow use of this method. Importantly, the error proneness of the polymerase in PCR is of no consequence in the present method as the amplification is merely being used to generate a detectable signal (measurable amount of DNA). The expected frequency of errors in the PCR product would not affect the measurement.

Selection of the restriction enzyme or enzymes used in this method depends upon several factors. First, the requisite restriction site must flank the sequence to be tested. Two non-identical restriction sites, recognized by different restriction endonucleases, may be selected. However, the enzyme(s) must not cut between the site of interest (bearing the mutation, heterozygosity or polymorphism) and the primer site or sites. The restriction sites should be selected such to yield a fragment of appropriate length. Such a fragment is preferably as short as possible to avoid possibility of having distal from the site of interest (a) a chance polymorphic sequence or (b) internal secondary structure which could act as a mismatch or a mispairing. On the other hand, the fragment should be of sufficient length to: (1) hybridize with the requisite specificity to form a heteroduplex bindable to an immobilized MBP; (2) include the site of interest and one or two primer sites; (3) be detectable following a convenient amount of amplification. Thus, such a fragment can be of any length but is preferably from about 50–500 bases, more preferably from about 100 to 300 bases. The primer site(s) of the test fragment can either be separate from, or overlap with, the sequence of interest.

The foregoing method is especially well-suited for detection of mutations in specific regions of DNA and is very amenable to automation whether employing PCR or ligase chain reaction, or only a single round of DNA synthesis to generate a detectable product.

DETECTION OF TRIPLET REPEATS

Figure 8:
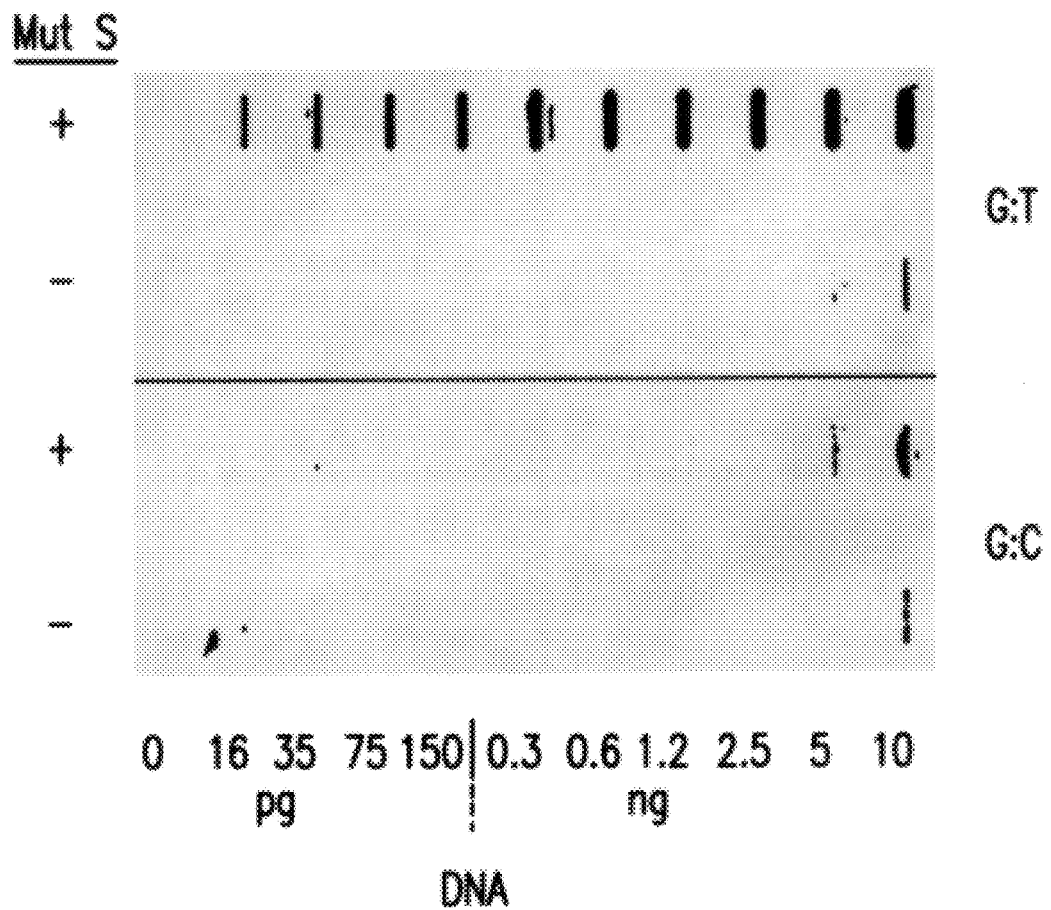
FIG. 8 shows the of binding of DNA preparations to MutS immobilized on nitrocellulose as part of a comparison with binding to soluble MutS.

The underlying cause of the large expansions of trinucleotide repeats may be the formation of a secondary structure in the template strand, in particular, a hairpin structure with a repeating block of G:C base pairs flanking a mismatch (A//A, T//T, C//C or G//G). Such a structure might be expected to block DNA synthesis. If so, polymerase idling (i.e., back and forth movement) may occur at the site of the hairpin resulting in the production of a single stranded loop (FIG. 8). If DNA synthesis can then resume across, or through, the hairpin, the result could be a large expansion of the repeat block in a single S-phase.

The differential ability of complementary heteroduplexes (CGG vs. CCG and CTG vs. CAG) to form secondary structures which bind to immobilized MBPs such as MutS is described in the Examples below and provides a basis for development of a rapid diagnostic test. Such a test detects the presence of expanded or contracted blocks of triplet repeats and the diseases associated with such repeats. The diagnostic test is used to identify individuals with (a) a mutation and who are at risk for developing a disease associated with triplet repeats before the onset of disease symptoms (e.g., prenatally) and (b) asymptomatic carriers of premutational alleles. The term "premutational" as used herein (see: Caskey et al., 1992, supra) refers to normal symptom free individuals who nevertheless transmit a disease condition, such as fragile X syndrome, and who have numbers of triplet repeats outside the normal range (e.g., 52–200 CGG repeats in fragile X syndrome). Fragile X syndrome is the first human disorder in which premutation DNA sequences in the parent predict risk of disease in the progeny. The present method therefore provides a means for screening parents for risk of transmitting fragile X syndrome (or other triplet repeat-associated disorders). As described herein, the assay is simple, reliable and does not require sequencing or the use or interpretation of any gel patterns.

The method is based on two discoveries by the present inventor. First, only one triplet repeat sequence of the complementary

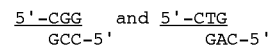

sequences is able to form partially double stranded secondary structures detectable by binding to an MBP. Second an immobilized MBP selectively binds duplexes such as those shown above (5'CGG$_n$ and 5'CTG$_n$ duplexes) but not duplexes of the forms 5'CCG$_n$ and 5'CAG$_n$ due to the formation of the double stranded secondary structure.

The assay method involves the following steps:
1. Test DNA is prepared and may be amplified if desired. If amplification is by PCR, the primers are selected to flank the triplet repeat region.
2. Test DNA (or amplified test DNA) is mixed with a labeled (e.g., biotinylated) single stranded probe complementary to the CGG- or CTG-containing strand in the triplet repeat region of the test DNA. The probe includes the flanking region sequences. In one embodiment, the number of triplet repeats in the probe is equal to the number of triplet repeats in the largest triplet repeat block considered to be normal. Repeat numbers fall into three classes: (1) normal, (2) premutational and (3) disease.
3. The mixture is denatured, preferably by heating or with pH treatment and allowed to reanneal.
4. The annealed DNA is exposed to immobilized MBP, preferably E. coli MutS, and the binding is visualized, preferably by the Enhanced Chemiluminescence method described herein. Alternatively, binding may be visualized using the in situ preamplification method described above.

If the test DNA contains only normal DNA, that is, DNA having a triplet repeat number equal to or lower than the triplet repeat number in the probe, there will either be no unpaired bases or the unpaired bases will be from the probe DNA. Because, the MBP does not recognize unpaired bases (single stranded region) of the CCG or CAG repeats found in the probe, the MBP will not bind to the annealed duplexes.

If, however, the test DNA has a block of triplet repeat sequences longer than that in the probe, the unpaired bases (CGG or CTG) of the test DNA, which do form secondary structure containing mismatches (i.e., heteroduplex secondary structure) will be recognized by the MBP.

Figure 11:
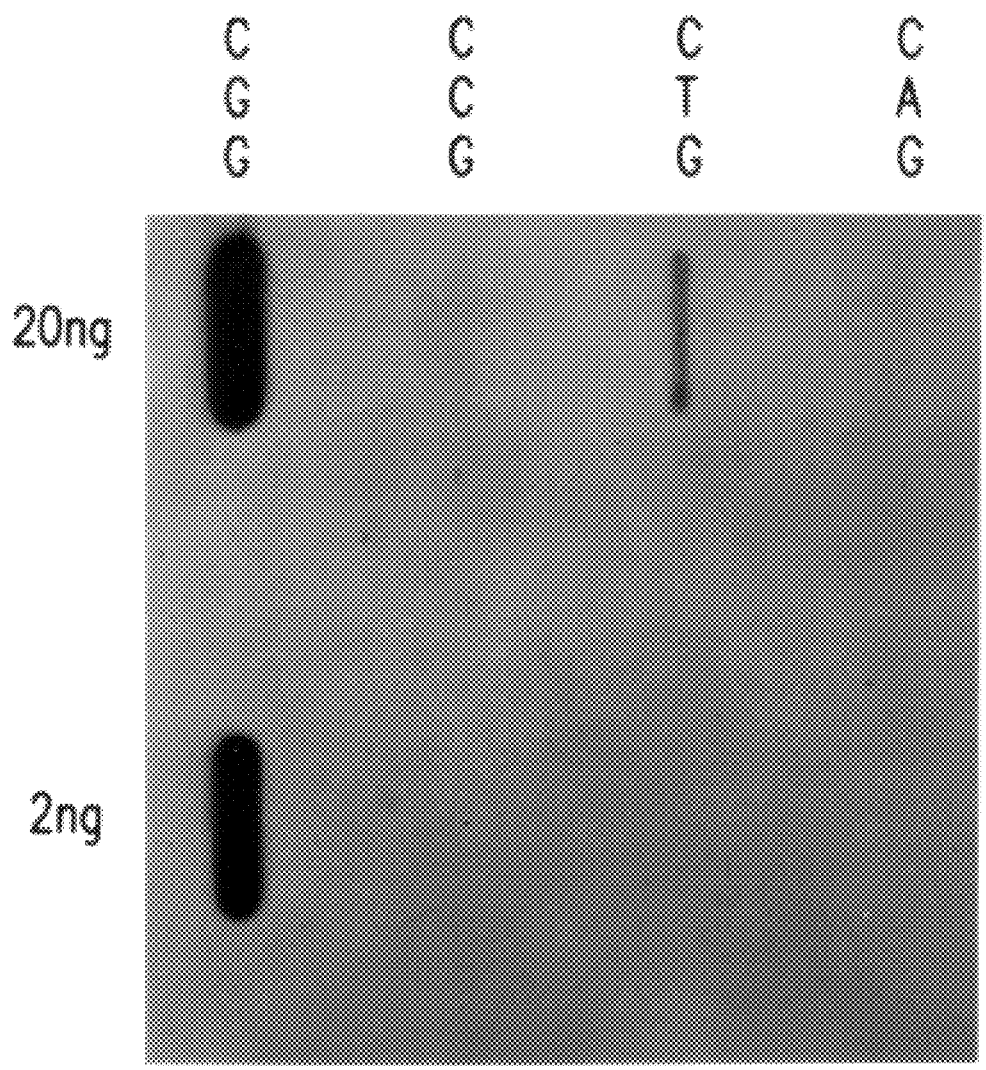
FIG. 11 shows the results of an immobilized mismatch binding protein assay of single stranded and double stranded triplet repeat block sequences. CCG: Single-stranded biotinylated $CCG_{10}$ 30 mer. CGG: Single stranded biotinylated $CGG_{10}$ 30 mer. CCG/CGG: Annealed double-stranded biotinylated $CCG_{10}/CGG_{10}$ 30 mer. Column A: 1.3 ng DNA. Column B: 13 ng DNA. Exposure was for 30 sec.

By adjusting the number of triplet repeats in the probe, the assay can be designed to detect either a premutational state or a disease state. This is schematically illustrated in FIG. 11. Thus, in one embodiment, the repeat block in the probe is shorter than the shortest block to be detected. This probe preferably contains 5'CCG repeats, or, read in the opposite polarity, 5'CGG repeats in the test DNA. Alternatively, this probe can contain 5'CAG repeats for detecting 5'GTC repeats in the test DNA. When the repeat block in the test DNA is shorter than in the probe, a looping out of probe DNA occurs, which is not recognized by the MBP. However, when the repeat block of the test DNA is longer than the probe, a looping out of test DNA occurs, which due to the 5'GGC repeat unit, forms a mismatch containing secondary structure which is recognized by the MBP.

In another embodiment, the repeat block in the probe is longer than the longest block to be detected. This probe preferably contains CGG repeats for detecting CCG (or, read in the opposite direction, GCC) repeats in the test DNA. Alternatively, this probe can contain CTG repeats for detecting CAG repeats in the test DNA. Thus, when the test block is shorter than the probe block, looping out occurs in the probe DNA which, due to the CGG repeat unit, forms a mismatch containing secondary structure which is recognized by the MBP. If the test DNA repeat block is longer than the probe block, the looping out occurs in the test DNA, which, due to the CCG unit sequence, does not form a structure that is recognized by the MBP.

As is readily apparent to those skilled in the art, this method for detecting repeat blocks is not limited to triplet repeats, but can be utilized with any microsatellite repeat number by appropriate design of the probe block sequence and length.

KITS

The present invention is also directed to a kit or reagent system useful for practicing the methods described herein. Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise (1) an immobilizable or immobilized MBP or functional derivative, preferably mutS, and (2) additional reagents useful in carrying out the assay. The kit may optionally contain labeled mismatch-containing oligonucleotides. For detecting a particular mutation, a kit may also contain labelled primers for carrying out a PCR. For detecting triplet repeats, the kit will contain the appropriate repeat-containing probes. A kit according to the present invention can additionally include ancillary chemicals such as the buffers and components of the solution in which binding of nucleic acid duplexes to the immobilized MBP takes place.

A kit useful for the method which detects mismatches by amplification of DNA bound to an immobilized MBP preferably contains restriction enzymes for preparing the test DNA fragments, wild-type genomic DNA fragments containing the sequence of interest, one or two primers for amplification of bound fragments, and positive and negative control double stranded DNA fragments either containing or lacking a detectable mismatch. Also included in such a kit would be the immobilized or immobilizable MBP and other reagents for the assay as described above.

Having now generally described the invention, the same will be more readily understood through reference to the following examples which are provided by way of illustration, and are not intended to be limiting of the present invention, unless specified.

EXAMPLE I

Binding of Mismatch-Containing DNA by Immobilized Mismatch Binding Protein

A. Materials and Methods

1. Preparation of immobilized MBP

A nitrocellulose sheet (0.45 $\mu$m, Schleicher & Schull) was wet with reaction buffer (20 mM Tris pH 7.6, 0.01 mM EDTA, 5 mM $MgCl_2$, 0.1 mM DTT) and placed in a dot blot apparatus (Bio-Rad).

Purified MBP, *E. coli* MutS, at a concentration of 0.5 $\mu$g/10 $\mu$l reaction buffer was spotted on the nitrocellulose paper in each well. The wells were incubated at room temperature, and the remaining liquid was pulled through with vacuum. Each well was washed twice with 100 $\mu$l reaction buffer by adding the solution to the well and then pouring it out. After the second wash, the remaining solution was pulled through the vacuum.

2. Blocking

The nitrocellulose filter was blocked with bovine serum albumin (BSA) to prevent the binding of other proteins or nucleic acids. Reaction buffer (200 $\mu$l) containing 1% (w/v) BSA was added to each well. After 1 hour at room temperature, the solution was poured out and each well washed with 2×100 $\mu$l reaction buffer by adding the solution to the well and then pouring it out. After the second wash, the remaining liquid was pulled through with vacuum.

3. Oligonucleotides The sequence of the oligonucleotides used in these studies was taken from the 30 base region surrounding the site of the sickle cell mutation in the human β-globin gene. The mismatch is at the site of the sickle cell mutation, although the mutant sequence used to form the mismatch is not the sickle cell mutation (the actual sickle cell mutation is an A:T→T:A transversion. Biotinylated oligonucleotides were biotinylated on the 5' end of the mutant strand. Biotinylation is accomplished during synthesis by adding a biotin-modified nucleotide to the 5' end of the oligonucleotides.

No Mismatch:
Mutant GCACCTGACTCCTGGGGAGAAGTCTGCCGT [SEQ ID NO:1]
Mutant CGTGGACTGAGGACCCCTCTTCAGACGGCA [SEQ ID NO:2]

G:T Mismatch:
Mutant GCACCTGACTCCTG<u>G</u>GGGAGAAGTCTGCCGT [SEQ ID NO:1]
Wild-type CGTGGACTGAGGAC<u>T</u>CCTCTTCAGACGGCA [SEQ ID NO:3]

4. Binding DNA

Biotinylated oligonucleotides, in 20 μl reaction buffer containing 1% BSA, were added to each well. After 30 minutes at room temperature, remaining liquid was poured out. Each well was washed with 5×100 μl reaction buffer by adding the solution to the well and then pouring it out. After the fifth wash, the remaining solution was pulled through by vacuum.

5. Binding Streptavidin-conjugated Horse Radish Peroxidase (HRP)

The presence of biotin was detected by its binding of Streptavidin. A 100 μl volume of Streptavidin-conjugated HRP (Pierce Chemicals) at a concentration of 50 mg/ml in reaction buffer +1% BSA was added to each well. After 2 hours at room temperature, the solution was poured out and each well washed with 5×100 μl reaction buffer by adding the solution and then pouring it out. After the fifth wash, the remaining solution was pulled through with vacuum.

6. Enhanced ChemiLuminescence® (ECL) Development

The nitrocellulose sheet was removed from dot blot apparatus and washed 3 times in a petri dish with 10 ml reaction buffer. Five ml ECL development solution (Amersham) was poured over the nitrocellulose. The substrate for HRP in this reagent is a chemiluminescent compound. After 1 minute, the solution was removed. The nitrocellulose was blotted dry and placed between 2 clear plastic sheets. The nitrocellulose thus protected was exposed to X-ray film in the dark for varying periods of time. In the experiments reported here, the exposure time was 1 minute.

7. Competition

In competition studies, the DNA binding was as described above, except that a constant amount of biotinylated mismatch-containing oligonucleotide (5 ng) was mixed with varying amounts of unlabeled DNA, with or without a mismatch, and added to the wells.

B. Results

1. Specific binding of mismatch-containing DNA by immobilized MBP

FIG. 1 shows the results (in duplicate) of adding increasing amounts of biotinylated mismatch-containing DNA (upper 2 lines) or mismatch-free DNA (lower 2 lines).

The immobilized MBP can detect as little as 0.2 ng of mismatch-containing 30-mer, whereas no detectable binding of mismatch-free 30-mer was observed even with 200 ng of DNA. (The lines around the lower spots were artifacts of incomplete washing.)

2. Competition Assay

Figure 2:
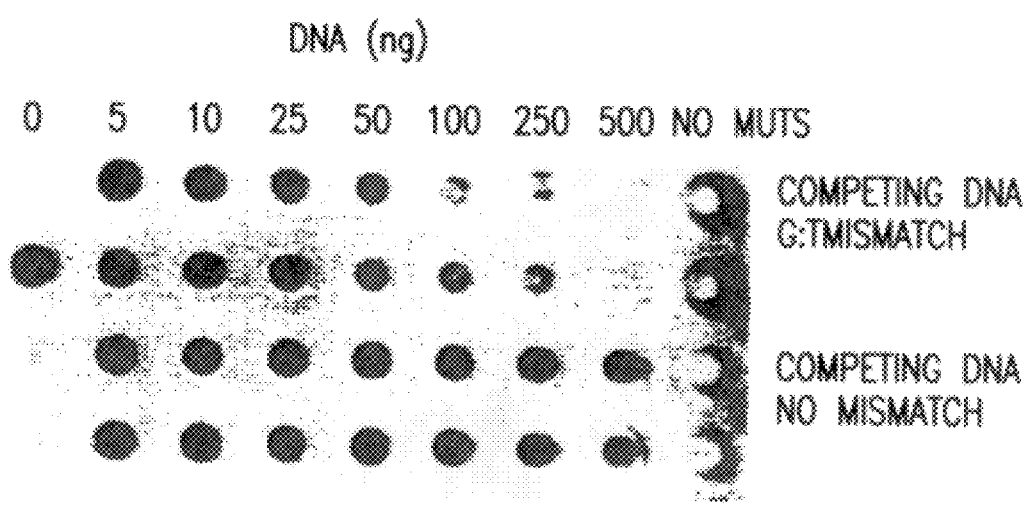
FIG. 2 shows the results of a competition assay of mismatched duplexes using nitrocellulose-bound MutS protein. Increasing amounts of unlabeled mismatch-containing 30-mer (upper 2 lines) or mismatch-free 30-mer (lower 2 lines) were added to 5 ng biotinylated mismatch-containing 30-mer. The far right column on the figure represents wells which contained no MutS.

FIG. 2 shows the results (in duplicate) of adding increasing amounts of unlabeled mismatch-containing 30-mer (upper 2 lines) or mismatch-free 30-mer (lower 2 lines) to 5 ng biotinylated mismatch-containing 30-mer. Although competition was clearly visible with 50 ng of mismatch-containing DNA, the mismatch-free DNA did not compete until 500 ng, if at all. The far right column on the figure contains no MBP.

The results indicate that, at least with the 30 mers used above, immobilized MBP discriminates between mismatch-containing and perfectly paired DNA with an efficiency of at least three orders of magnitude. Similar results have been obtained using 54 mers with a sequence derived from the V3 loop of HIV. Therefore, even if the discrimination decreases as the amount of perfectly paired duplex increases, the discrimination efficiency when using 300 mers, considered to be the maximum useful length for polymorphism studies of the human genome, should be on the order of a factor of 100.

EXAMPLE II

Detection of Various Single Base Mismatches Unpaired Bases

This study was performed to ascertain the ability of immobilized *E. coli* MutS protein to bind to and detect various single base mismatches and one to four unpaired bases.

These studies utilized synthetic oligonucleotides (eight 30 mers and one each of a 31 mer, a 32 mer a 33 mer and a 34 mer) listed below:

| | SEQ ID NO: |
|---|---|
| 5' GCACCTGACTCCTG<u>G</u>GGAGAAGTCTGCCGT 3' | 1 |
| 3' CGTGGACTGAGGAC<u>C</u>CCTCTTCAGACGGCA 5' | 2 |
| 3' CGTGGACTGAGGAC<u>T</u>CCTCTTCAGACGGCA 5' | 3 |
| 5' GCACCTGACTCCTG<u>T</u>GGAGAAGTCTGCCGT 3' | 4 |
| 3' CGTGGACTGAGGAC<u>G</u>CCTCTTCAGACGGCA 5' | 5 |
| 5' GCACCTGACTCCTG<u>C</u>GGAGAAGTCTGCCGT 3' | 6 |
| 5' GCACCTGACTCCTG<u>A</u>GGAGAAGTCTGCCGT 3' | 7 |
| 3' CGTGGACTGAGGAC<u>A</u>CCTCTTCAGACGGCA 5' | 8 |
| 3' CGTGGACTGAGGACC<u>C</u>CCTCTTCAGACGGCA 5' | 9 |
| 3' CGTGGACTGAGGACC<u>CA</u>CCTCTTCAGACGGCA 5' | 10 |
| 3' CGTGGACTGAGGACC<u>CAG</u>CCTCTTCAGACGGCA 5' | 11 |
| 3' CGTGGACTGAGGACC<u>CAGG</u>CCTCTTCAGACGGCA 5' | 12 |

The nucleotide or nucleotides participating in the mismatches (or unpaired bases) are underscored above. The homoduplex and heteroduplexes containing the mismatches or unpaired bases, prepared from the above oligonucleotides are indicated below.

Homoduplex

5' Biotin- GCACCTGACTCCTGGGGAGAAGTCTGCCGT -3'    (SEQ ID NO:1)
       3'- CGTGGACTGAGGACCCCTCTTCAGACGGCA -5'    (SEQ ID NO:2)

G//T Mismatch

5' Biotin- GCACCTGACTCCTGGGGAGAAGTCTGCCGT -3'    (SEQ ID NO:1)
       3'- CGTGGACTGAGGACTCCTCTTCAGACGGCA -5'    (SEQ ID NO:3)

T//G Mismatch

5' Biotin- GCACCTGACTCCTGTGGAGAAGTCTGCCGT -3'    (SEQ ID NO: 4)
       3'- CGTGGACTGAGGACGCCTCTTCAGACGGCA -5'    (SEQ ID NO:5)

C//T Mismatch

5' Biotin- GCACCTGACTCCTGCGGAGAAGTCTGCCGT -3'    (SEQ ID NO:6)
       3'- CGTGGACTGAGGACTCCTCTTCAGACGGCA -5'    (SEQ ID NO:3)

G//G Mismatch

5' Biotin- GCACCTGACTCCTGGGGAGAAGTCTGCCGT -3'    (SEQ ID NO:1)
       3'- CGTGGACTGAGGACGCCTCTTCAGACGGCA -5'    (SEQ ID NO:5)

A//G Mismatch

5' Biotin- GCACCTGACTCCTGAGGAGAAGTCTGCCGT -3'    (SEQ ID NO:7)
       3'- CGTGGACTGAGGACGCCTCTTCAGACGGCA -5'    (SEQ ID NO:5)

G//A Mismatch

5' Biotin- yGCACCTGACTCCTGGGGAGAAGTCTGCCGT -3'   (SEQ ID NO:8)
       3'-CGTGGACTGAGGACACCTCTTCAGACGGCA    -5'  (SEQ ID NO:8)

A//C Mismatch

5' Biotin- GCACCTGACTCCTGAGGAGAAGTCTGCCGT -3'    (SEQ ID NO:7)
       3'- CGTGGACTGAGGACCCCTCTTCAGACGGCA -5'    (SEQ ID NO:2)

A//A Mismatch

5' Biotin- GCACCTGACTCCTGAGGAGAAGTCTGCCGT -3'    (SEQ ID NO:7)
       3'- CGTGGACTGAGGACACCTCTTCAGACGGCA -5'    (SEQ ID NO:8)

T//T Mismatch

5' Biotin- GCACCTGACTCCTGTGGAGAAGTCTGCCGT -3'    (SEQ ID NO:4)
       3'- CGTGGACTGAGGACTCCTCTTCAGACGGCA -5'    (SEQ ID NO:5)

C//C Mismatch

5' Biotin- GCACCTGACTCCTGGCGAGAAGTCTGCCGT -3'    (SEQ ID NO:)
       3'- CGTGGACTGAGGACCCCTCTTCAGACGGCA -5'    (SEQ ID NO:2)

Unpaired C

5' Biotin- GCACCTGACTCCTGG GGAGAAGTCTGCCGT -3'
       3'- CGTGGACTGAGGACCCCCTCTTCAGACGGCA -5'   (SEQ ID NO:9)

Unpaired CA

5' Biotin- GCACCTGACTCCTGG  GGAGAAGTCTGCCGT -3'
       3'- CGTGGACTGAGGACCCACCTCTTCAGACGGCA -5'  (SEQ ID NO:10)

Unpaired CAG

5' Biotin- GCACCTGACTCCTGG   GGAGAAGTCTGCCGT -3'
       3'- CGTGGACTGAGGACCCAGCCTCTTCAGACGGCA -5' (SEQ ID NO:11)

Unpaired CAGG

5' Biotin- GCACCTGACTCCTGG    GGAGAAGTCTGCCGT -3'
       3'- CGTGGACTGAGGACCCAGGCCTCTTCAGACGGCA -5' (SEQ ID NO:12)

As described above, these sequences were taken from, or are closely related to, the human β-globin gene in the region of the mutation responsible for sickle-cell anemia. The mismatches are at position 15 and the unpaired bases are between positions 15 and 16 of the oligonucleotides.

Biotin Labeling of DNA

Those oligonucleotides beginning with the sequence 5'GCA were prepared with a 5' biotin label to allow detection by the Enhanced Chemiluminescence (ECL) detection system and were annealed to unlabeled oligonucleotides such that only one strand of each duplex was labeled.

Some oligonucleotides were labeled with both biotin and $^{32}$P, which did not affect either biotin or radioactivity detection.

The duplexes were used in a mismatch detection assay using immobilized mismatch binding protein (MutS), essentially as described above. The following is a description of the assay:

Oligonucleotides were diluted in TNE buffer (10 mM Tris HCl, pH 8.0; 0.01 M NaCl, 1 mM EDTA). Biotin labeled or radiolabeled oligonucleotides were diluted to 10 ng/μl and unlabeled oligonucleotides to 100 ng/μl. Equal volumes of diluted oligonucleotides were mixed and annealed at 70° C. for 10 min, followed by incubation at room temperature for 30 min, followed by quenching on ice. The preparations were stored at −20° C. where appropriate. The unlabeled oligonucleotides were in 10-fold excess to assure that all biotin-labeled strands were in duplexes.

Immobilization of MutS on Solid Supports and Biotin Detection Assay (a) Nitrocellulose A nitrocellulose sheet (0.45 μm, Schleicher and Schull, BA85) was pre-wet by floating in reaction buffer (20 mM Tris HCl, pH 7.6; 5 mM MgCl$_2$, 0.1 mM DTT, 0.01 mM EDTA). MutS (500 ng/well) in reaction buffer was bound to the nitrocellulose in a 48 well slot blotting apparatus (Hoefer Scientific Instruments) over 3 sheets of blotting paper (Schleicher and Schull GB002). Reaction buffer alone was added to "no MutS" wells. After 20 min. at room temperature, nitrocellulose was blocked with 200 μl/well of 3% horse radish peroxidase (HRP)-free bovine serum albumin (BSA). After 1 hour, excess blocking solution was pulled through with vacuum and DNA (1 ng and 10 ng) was added in 20 μl reaction buffer containing 3% BSA. After 30 min. at room temperature, wells were washed 5 times with 100 μl reaction buffer. The wash fluids were decanted rather than pulled through with vacuum.

(b) Detection of Biotin

The presence of biotin-labeled DNA bound on the nitrocellulose sheet was detected by visualizing the binding of streptavidin to biotin. 100 μl streptavidin-conjugated HRP (0.05 μg/ml in reaction buffer+BSA) was added to each well. After 20 min. at room temperature, any remaining solution was decanted and the wells washed 5 times with 100 μl reaction buffer as above.

The nitrocellulose sheet was removed from the apparatus and washed 4 times for 1 min with 50 ml reaction buffer in a small tray. Nitrocellulose was blotted dry and immersed in 10 ml of ECL development solution (Amersham).

Results

Figure 3A:
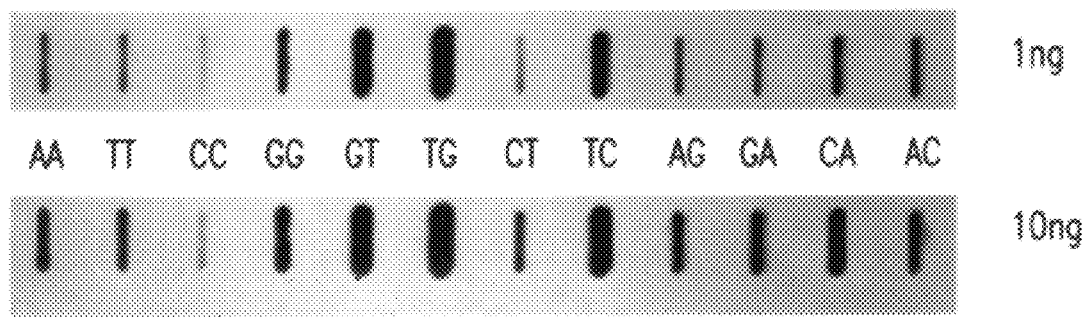
FIG. 3 shows the binding of immobilized E. coli mutS to various duplexes containing mismatched and unpaired bases. Mismatch containing heteroduplexes are labeled GT, GG, etc., with the two concentrations of DNA tested (1 or 10 ng) indicated. Heteroduplexes containing unpaired bases were labeled as follows: [1]: Unpaired C; [2]: Unpaired CA; [3]: Unpaired CAG; [4] Unpaired CAGG. Asterisks next to the mismatched base pair or the number label for the unpaired bases indicates "No MutS" controls.
Figure 3B:
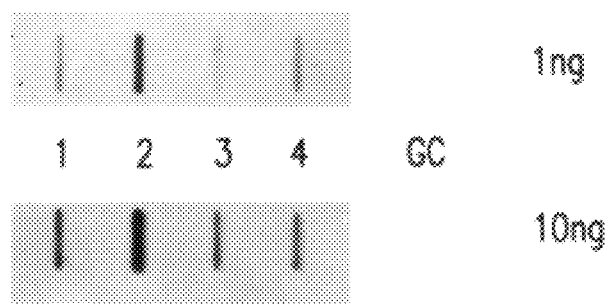

The results are presented in FIG. 3. Mismatch containing heteroduplexes are labeled GT, GG, etc., with the two concentrations of DNA tested (1 or 10 ng) indicated. Heteroduplexes containing various numbers of unpaired bases were labeled with the number of unpaired bases as follows: [1]: Unpaired C; [2]: Unpaired CA; [3]: Unpaired CAG; [4] Unpaired CAGG.

All mismatches except C//C were detected under these conditions. Heteroduplexes with 1–4 unpaired bases were detected, though heteroduplexes with 3–4 unpaired bases were not detected as well as 1–2 unpaired bases.

The fact that T//C mismatches were better detected than C//T mismatches suggested that the sequence of the neighboring bases on an individual strand may influence the extent of mismatch detection, at least in relatively short oligonucleotides such as those used here. However, G//T and T//G mismatches were equally well-detected, suggesting that well-detected mismatches are detected independent of strand orientation.

The failure to bind C//C mismatches does not diminish the utility of this method for mutation detection, since every wild-type/mutant pairing gives rise to two different mismatches, for example G//G - C//C, wherein G//G mismatches give strong signals.

These results indicate that immobilized mismatch binding protein assays, as disclosed in the instant patent application, detect all mutations due to a single base change. Thus, although the C//C mismatches were not bound by immobilized MutS, the corresponding G//G mismatch, which would of necessity occur in any mutant:wild type pairing that had a C//C mismatch, gave a strong signal. Therefore this method may be used to detect all mutations arising from a single base change as well as mutations arising from small (1–4 nucleotide) additions or deletions.

EXAMPLE III

Detection of Heterozygosity

The present methods were used to detect heterozygosity at a specific location in human genomic DNA. PCR amplification was performed on a portion of exon 3 of the human glucokinase gene extending from codon 98 (encoding glutamine) to the stop codon (Soffel et al., Proc. Natl. Acad. Sci. USA 89:7698–7702 (1992)). The wild-type double stranded sequence of 100 bases corresponding to exon 3 human glucokinase is as follows:

5'- GCACTAACTTCAGGGTGATGCTGGT-GAAGGTGGGAGAAGG

3'- CGTGATTGAAGTCCCACTACGACCACT-TCCACCCTCTTCC

TGAGGAGGGG
CAGTGGAGCGTGAAGACCAAACACCAGATG
ACTCCTCCCC
GTCACCTCGCACTTCTGGTTTGTGGTCTAC
ATGAGGTAGGGGCTCCTGCG -3' [SEQ ID NO:13]
TACTCCATCCCCGAGGACGC -5'

In the heterozygous DNA (see below), the C of the underlined CAG codon was mutated to T. The DNA sequences tested were PCR amplified from genomic DNA obtained from: (1) a known heterozygote at that position [labeled "Heterozygote", (2) a known homozygote at that position [labeled "Homozygote 1"] and (3) a presumed homozygote at that position [labeled "Homozygote 2"]. Test DNAs were denatured, by heating, allowed to reanneal and tested for the presence of mismatches (i.e., heterozygotes) by testing their binding in an immobilized mismatch binding protein assay according to the present invention, utilizing E. coli MutS.

PCR Amplification to Create 100 Mers

The templates used were:
(a) "HETEROZYGOTE"—DNA known to be heterozygous for a mutation (C:G to T:A) in glucokinase gene exon 3;
(b) "HOMOZYGOTE 1"—Human genomic DNA known to be homozygous at glucokinase gene exon 3;
(c) "HOMOZYGOTE 2"—Human genomic DNA, male, presumed homozygous at glucokinase gene exon 3 (commercially obtained from Sigma Chemical Co.)

The primers (obtained from Operon) were HPLC purified and had the following sequences, corresponding to the 5' termini of the two 100 mer strands shown above:

Primer #1: 5'(biotin)-GCACTAACTTCAGGGTGATG-3' [SEQ ID NO:14]

Primer #2: 5'-GCGTCCTCGGGGATGGAGTA-3'. [SEQ ID NO:15]

PCR Primer #1 contained biotin bound at the 5' end to allow detection in the ECL detection system described below. Primer #2 was radioactively labeled with a 5'-$^{32}$P-phosphate to allow quantitation of the different amplification products after removal of unused primers.

The PCR reaction included: 10 mM Tris HCl pH 8.3; 50 mM KCl; 1.5 mM MgCl$_2$; 0.001% gelatin (w/v); 0.05 mM dATP; 0.05 mM dTTP; 0.05 mM dGTP; 0.05 mM dCTP; 0.1 μM primer #1; 0.075 μM primer #2; 0.025 μM $^{32}$P primer #2; 200 ng template DNA; and 2.5 units AmpliTaq DNA polymerase (Perkin-Elmer). Reaction volume was 100 μl. Amplification was carried out for 30 cycles in a Perkin-Elmer thermocycler by denaturing at 90° C. for 1 min., annealing at 55° C. for 1 min. and extension at 72° C. 2 min. Unused primers were removed by centrifugal dialysis using Centricon 30 (Amicon) microconcentrators according to manufacturers protocol. PCR products were quantitated by running equal amounts (measured as cpm of radioactivity) on non-denaturing 8% polyacrylamide gels, staining with ethidium bromide and comparing them to standard DNA.

PCR Amplification to Create 230 Mers

For the heterozygous 230 mer, the template (DGK79) was human genomic DNA known to be heterozygous for a mutation (GCC to TCC, Gly to Ser, at codon 53) in exon 3 of the glucokinase gene (obtained from Dr. N. Cohen, CEPH, Paris, France. The corresponding homozygous template was human genomic DNA presumed to be homozygous in exon 3 of the glucokinase gene (obtained from Sigma Chemical Co.)

PCR amplification was performed using three different polymerase enzymes:
1. *Pyrococcus woesii* (PWO) polymerase (Boehringer-Mannheim).
2. *Thermococcus litoralis* polymerase (New England Biolabs)
   a. Vent (exo$^-$) or
   b. Vent (exo$^+$) included exonuclease The primers for the 230 mers were:

Primer #1: 5'(biotin)-GAAGGTGATGAGACGGAT [SEQ ID NO:16]

Primer #2: 5'-CCCAGGAGATTCTGTCTC [SEQ ID NO:17]

PCR mixtures (100 μl) each contained: 20 mM Tris-HCl pH 8.8, 10 mM KCl, 2 mM MgSO$_4$, 10 mM (NH$_4$)$_2$SO$_4$, 0.1% Triton X-100, 0.25 mM dNTPs, 0.2 μM primer #1, 0.2 μM primer #2, 200 ng template DNA, 2 units DNA polymerase. 30 cycles were performed as follows: Denaturation: 1 min., 94° C. Annealing: 1 min., 3 cycles 64° C., 3 cycles 62° C., 3 cycles 60° C., 3 cycles 58° C., 3 cycles 56° C., 15 cycles 54° C. Extension was for 2 min. at 72° C. Primers were removed with QIA quick spin columns (Quigen). PCR products were eluted in 10 mM Tris-HCl pH 8.0 and were adjusted to 0.1 M NaCl. The denaturation was done at 100° for 2 min. Annealing was done at 55° C. for 60 min, 75° C. for 4 min, 55° C. for 30 min, followed by cooling to room temperature.

Additional 30 Mer Controls

Positive and negative control DNA, also studied in Example II, above, comprised 30 mer heteroduplexes with a G//T mismatch:

5'      Biotin-      GCACCTGACTCCTG
GGGAGAAGTCTGCCGT -3' (SEQ ID NO:1)
3'- CGTGGACTGAGGACT̲CCTCTTCAGACGGCA -5'
(SEQ ID NO:3)

and 30 mer homoduplexes having a G:C in the same position.

5'      Biotin-      GCACCTGACTCCTG
GGGAGAAGTCTGCCGT -3' (SEQ ID NO:1)
3'- CGTGGACTGAGGACC̲CCTCTTCAGACGGCA -5'
(SEQ ID NO:2).

(b) The immobilized MutS Binding assays were performed as described above. DNA was denatured and annealed (in Perkin-Elmer thermocycler) according to the following schedule: 100° C. for 4 min; 50° C. for 1 hour; 75° C. for 4 min; 50° C. for 30 min, followed by cooling to room temperature. MutS was added to each well of a slot blot apparatus, DNA preparations were added and the wells washed as described. Streptavidin-HRP was added and allowed to bind to any biotin present on the nitrocellulose, and detected by the ECL assay, as above.

Results

Figure 4:
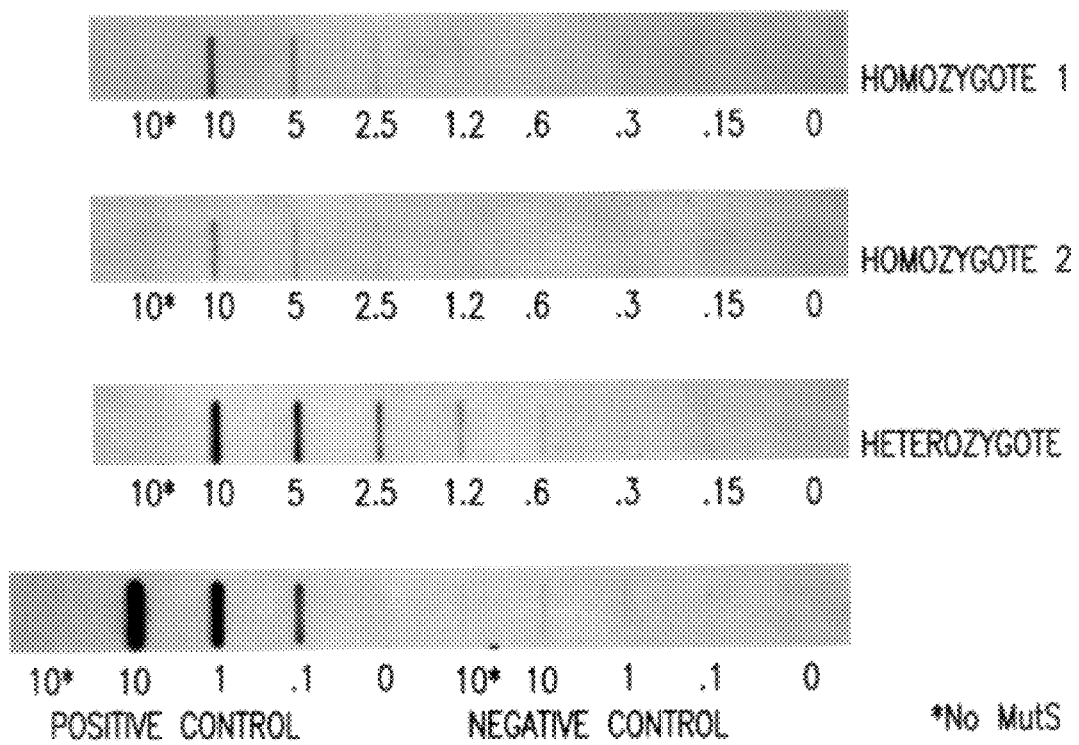
FIG. 4 shows the binding of homozygote and heterozygote DNA to immobilized MutS. The positive control was a G//T-containing 30-mer heteroduplex described above:
5' Biotin- GCACCTGACTCCTG GGGAGAAGTCTGCCGT -3' (SEQ ID NO:1)
3'- CGTGGACTGAGGACTCCTCTTCAGACGGCA -5' (SEQ ID NO:3)
The negative control was a 30-mer homoduplex described above containing a G:C match at the same position:
5' Biotin- GCACCTGACTCCTG GGGAGAAGTCTGCCGT -3' (SEQ ID NO:1)
3'- CGTGGACTGAGGACCCCTCTTCAGACGGCA -5' (SEQ ID NO:2)

The results binding of 100 mer DNA duplexes to immobilized MutS are shown in FIG. 4. The positive control was the G//T containing 30-mer heteroduplex. The negative control was the 30-mer homoduplex, as described above.

No binding of negative control was detected even at 10 ng of DNA, whereas the positive control was detected at 0.1 ng. The absence of binding without MutS indicates that all DNA binding observed was MutS-dependent. Binding of heterozygote nucleic acid to MutS was clearly visible at 0.6 ng. Homozygote binding (independent of the source of the DNA) was faintly detectable at 1.25 ng and was clearly detected at 2.5 ng. Thus, heterozygote DNA was detected as much as 5 times better than homozygote DNA in this assay. This is in contrast to the binding of MutS to the DNA in solution (see experiments described below). It was concluded from these and other results that the binding of mismatch containing DNA to immobilized MutS is markedly better than the binding to MutS in solution.

The binding of homozygote DNA at higher concentrations was considered to be the result of errors introduced during amplification by the Taq polymerase, a well-known phenomenon. Thus, such inappropriate binding still represented mismatch binding by the immobilized MutS.

The possibility that longer DNA fragments were bound by MutS regardless of the presence of mismatches is highly unlikely, because (a) the PCR products (100 base pairs) were only 3.3 times larger that the negative control DNA (30 base pairs) which did not bind, and (b) competition with a 100-fold excess of unlabeled undigested genomic DNA did not reduce "background" binding to the homozygote DNA.

Figure 5A:
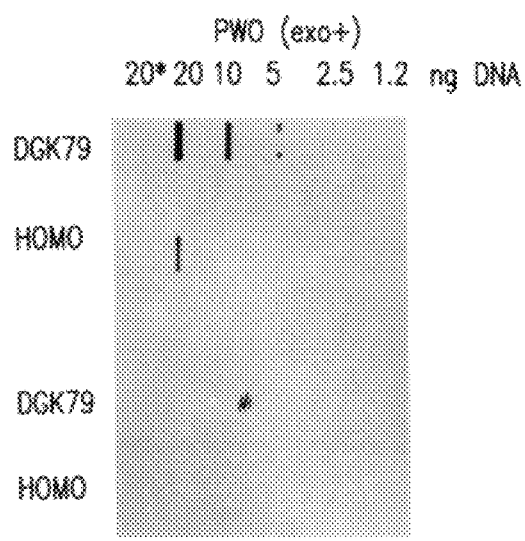
FIG. 5 shows the binding of PCR amplified homozygote and heterozygote 230 mer DNA duplexes to immobilized MutS. DGK79 refers to a heterozygous 230 mer containing a G//A and T//C mismatches. HOMO refers to the homoduplex 230 mer lacking any known mismatches. The DNA was amplified using three different polymerase preparations. Panel A shows results using PWO (exo+) (containing exonuclease). Panel B shows results using Vent (exo+) and Vent (exo−) (containing or lacking exonuclease activity, respectively). Panel C shows results with the positive and negative control 30 mers used in FIG. 4.
Figure 5B:
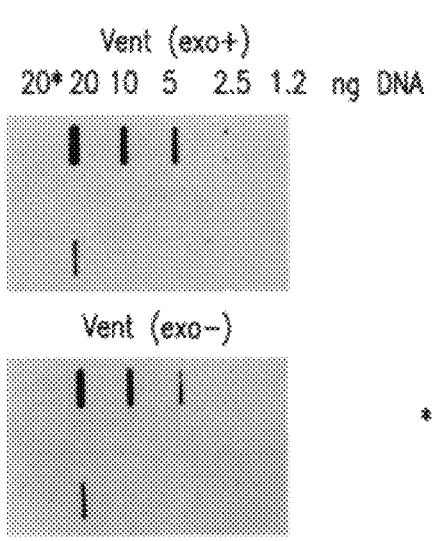
Figure 5C:
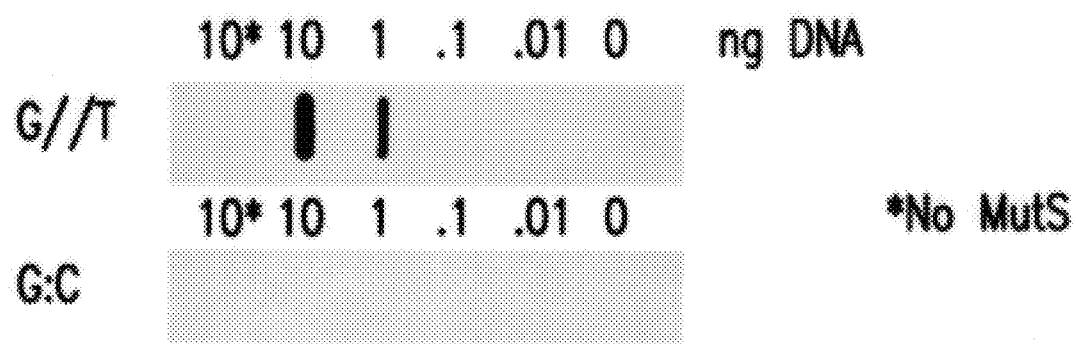

The results of binding of 230 mer DNA duplexes to immobilized MutS are shown in FIG. 5. 230 mer heteroduplexes are designated "DGK79," whereas 230 mer homoduplexes are designated "HOMO" in panels A and B. Panel C shows the positive control 30 mer heteroduplex ("G//T") and the negative control 30 mer homoduplex ("G:C").

The results indicate that heteroduplex molecules (having G//A and T//C mismatches) amplified by three different polymerase preparations (with or without exonuclease activity, bound to immobilized MutS with great specificity down to concentrations of 2.5 ng DNA. In contrast, only background binding of amplified homoduplexes was observed (at 20 ng DNA, possibly due in part to errors introduced during amplification. Binding of 30 mer heteroduplex and homoduplex DNA to immobilized MutS was as expected. These results provide further evidence of the sensitivity of the present assay and show strong binding of DNA having G//T, G//A and T//C mismatches.

EXAMPLE IV

Mismatch Binding by MutS Immobilized on Other Supports

A. MutS Immobilized on Polyvinylidene Difluoride (PVDF)

Immobilization of MutS and assay of DNA binding was performed exactly as described above for nitrocellulose. The only change in the above protocol was the initial equilibration of the PVDF membrane. The membrane was slowly immersed in 100 ml ethanol and left for two minutes. The membrane was then washed five times with 100 ml distilled water. The membrane was floated on 100 ml reaction buffer and then immersed. The PVDF membrane was then equilibrated to the reaction buffer for 10 minutes prior to use.

Figure 6:
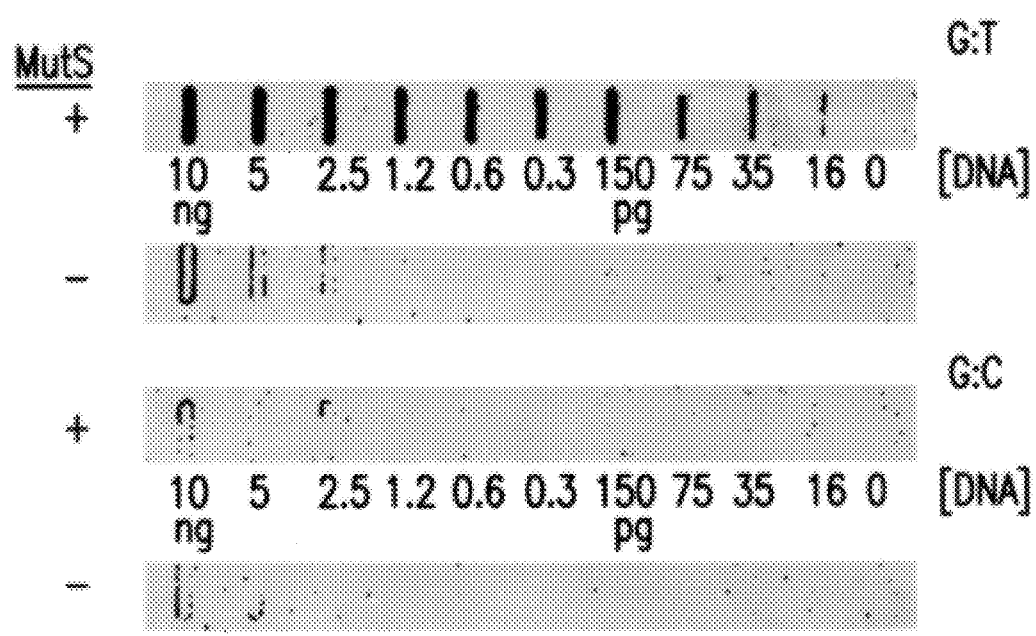
FIG. 6 shows the binding of mismatch containing DNA by MutS immobilized on PVDF. This study utilized the biotin label and the ECL assay.

The results are shown in FIG. 6. This study utilized the biotin label and the ECL assay as described in Examples I–III. Slots to which were bound 500 ng MutS could detect from 10 ng down to 16 pg of G//T containing 30 mer DNA. G:C containing 30 mers were not detected at any concentration tested. Control slots having no MutS did not bind any DNA. The "no MutS" controls as well as the MutS—G:C combination showed halos surrounding the slots, in contrast to typical dark zones of reactivity in the slots, at the two or three higher concentrations. These halos are believed to be artifacts. However, even if there were binding of G:C detected at 2.5 ng DNA, the binding of the mismatched DNA is at least 128-fold greater.

It was concluded from this experiment that MutS immobilized on PVDF functions in accordance with the invention in binding mismatch containing DNA heteroduplexes.

B. MutS Immobilized on Nylon

Nylon filter was pre-wet with reaction buffer (as above). The slot blot apparatus was assembled as above. Reaction buffer, 100 µl/well was added and pulled through with vacuum. MutS was applied to each well (500 ng in 10 µl per well). "No MutS" controls contained 10 µl of reaction buffer. The filters were incubated for 15 min at room temperature and were then blocked as above. The apparatus was sealed with Parafilm.

This study utilized a $^{32}$P label rather than biotin label and assayed bound radioactivity (by radioautography). $^{32}$P labeling was achieved using a kinase reaction. The kinase reaction mix contained: 70 mM Tris HCl, pH 7.6; 10 mM MgCl$_2$; 5 mM DTT; 20 µCi $^{32}$P-ATP; 30 units T4 polynucleotide kinase; and 500 ng DNA (in the case of primer #2). The kinase reaction was performed in a 20 µl reaction volume at 37° C. for 30 min. Kinase was inactivated by heating at 65–70° C. for 10–15 min. DNA was stored at –20° C.

$^{32}$P-labeled DNA was prepared in reaction buffer containing 3% BSA. Samples of 20 µl were pipetted into appropriate wells and incubated for 30 min. at room temperature. Wells were washed with 150 µl reaction buffer five times, with decanting, and the last wash was pulled through with vacuum. The filter was removed and washed with 50 ml reaction buffer 3 times. The filter was blotted dry, wrapped in Saran wrap. Radioautography was performed by exposing the filter to X-ray film overnight at –80° C. The film was then developed and the reaction zones visualized.

Figure 7:
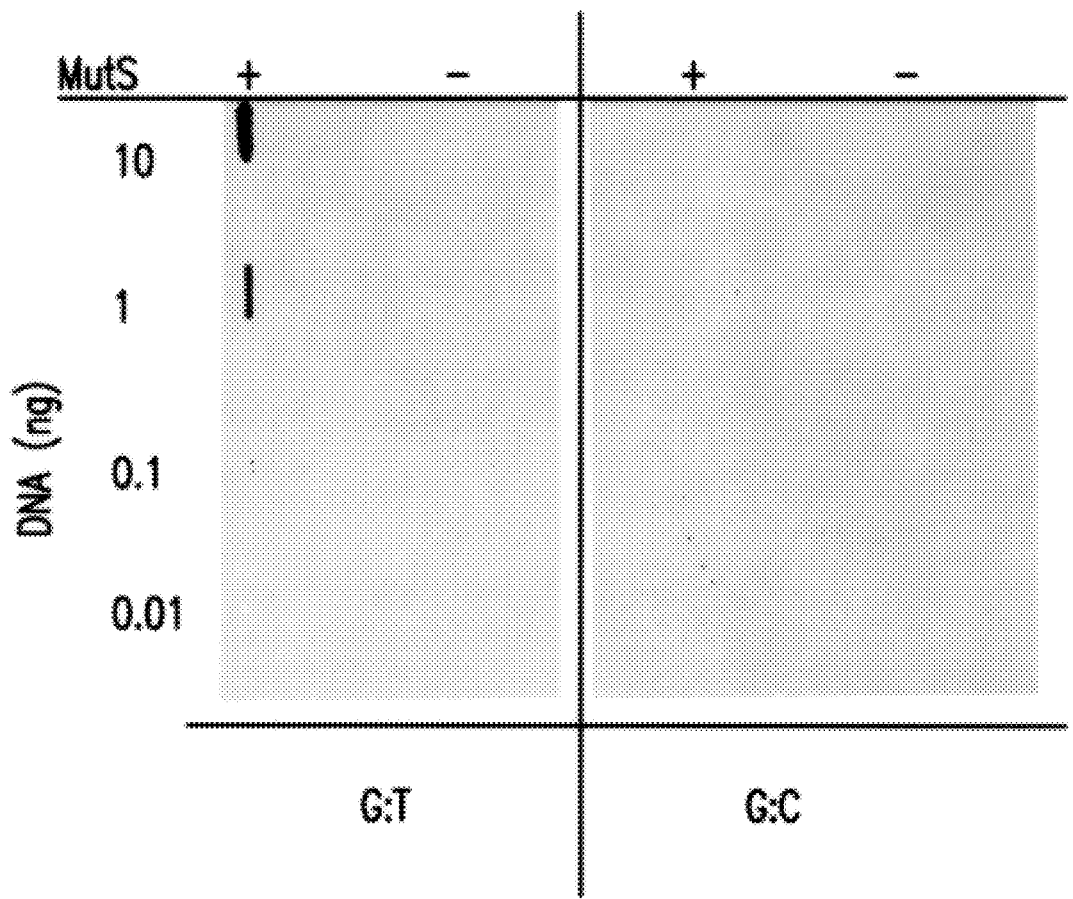
FIG. 7 shows the binding of mismatch containing DNA by MutS immobilized on nylon. This study utilized a $^{32}P$ label and assayed bound radioactivity (by radioautography). the 30-mers described under FIG. 4 were utilized. Control slots: no MutS.

The results are shown in FIG. 7. Slots to which were bound 500 ng MutS could detect from 10 ng down to 0.1 ng of G//T containing 30 mer DNA. G:C containing 30 mers were undetected at all four concentrations tested (10, 1, 0.1 and 0.01 ng). Control slots having no MutS did not bind any DNA.

It was concluded from this experiment that MutS immobilized on nylon functions in accordance with the invention in binding mismatch-containing DNA heteroduplexes.

C. MutS Immobilized to Magnetic Beads

Dynabeads (Dynal M-280, tosyl activated) were resuspended by vortexing and 2 mg of beads were taken for the assay. The beads were washed twice with 400 µl phosphate buffered saline (PBS) (140 mM NaCl, 2.7 mM KCl, 10 mM Na$_2$HPO$_4$, KH$_2$PO$_4$, pH 7.4), and the wash fluid was aspirated by pipet. 250 µg of beads were taken for the "No MutS" control and were incubated with 50 µl PBS supplemented with 3% BSA (PBS-BSA). To the remaining beads was added 235 µg MutS (ratio of 25 µg MutS/mg beads). These mixtures were incubated overnight at room temperature with shaking. The supernatants were then removed and the beads washed with 700 µl PBS-BSA, with shaking, as follows: three times for 10 minutes, once for 30 min and overnight at 4° C. Between washes, beads were allowed to settle and the supernatant removed by aspiration.

Beads were resuspended at 250 µg/100 µl PBS-BSA and dispensed in 250 µg aliquots. The supernatant was removed, varying concentrations of DNA were added in 400 µl PBS-BSA and the mixtures incubated for 30 min. at room temperature with shaking. The DNA solution was removed and the beads were washed 3 times with 600 µl reaction buffer (see Example II, above). 0.05% HRP-conjugated streptavidin in reaction buffer was added in a volume of 400 µl per tube and incubated for 20 min. at room temperature with shaking. The streptavidin solution was removed, the beads washed 3 times with 600 µl reaction buffer and 200 µl of developer was added, comprising 2.5 ml citrate acetate (10 mM citric acid, 100 mM sodium acetate, pH 6.0), 26 µl tetramethylbenzidine and 4.25 ml 3% H$_2$O$_2$. When color developed (3–15 min.), the reaction was stopped by adding 25 µl 2M sulfuric acid. Absorbance was read at a wavelength of 450 nm (OD$_{450}$).

TABLE I

Binding of 30 mer Heterozygous (Het) and Homozygous (Homo) DNA to MutS Immobilized on Magnetic Beads

| DNA (ng) | OD$_{450}$ (Absorbance Units) | | |
|---|---|---|---|
| | Homo | Het | Het (Net units)* |
| 1.6 | 0.005 | 0.021 | 0.017 |
| 3.12 | 0.003 | 0.013 | 0.009 |
| 6.25 | 0.005 | 0.018 | 0.015 |
| 12.5 | 0.003 | 0.040 | 0.036 |
| 25 | 0.004 | 0.060 | 0.056 |

TABLE I-continued

Binding of 30 mer Heterozygous (Het) and Homozygous (Homo)
DNA to MutS Immobilized on Magnetic Beads

| DNA (ng) | $OD_{450}$ (Absorbance Units) | | |
|---|---|---|---|
| | Homo | Het | Het (Net units)* |
| 50 | 0.002 | 0.107 | 0.103 |
| 100 | 0.005 | 0.101 | 0.097 |

*After subtraction of Background (0.004 units) which was the mean of the following two controls:
No DNA: 0.005
No MutS 0.004 (using 100 ng Het DNA)

These results show a linear relationship between DNA concentration added to the immobilized MutS beads and the amount of DNA bound ($OD_{450}$) between 1.6 and 50 ng DNA, at which level DNA binding achieved a plateau. Homozygous DNA showed no binding whatsoever to MutS immobilized on the magnetic beads.

It was concluded that MutS immobilized on magnetic beads binds mismatch-containing DNA with high specificity.

EXAMPLE V

Comparison of Mismatch Binding by Immobilized and Soluble MutS

This study compared binding of a G//T-containing heteroduplex (30 mer described above) to MutS immobilized on nitrocellulose and compared it to binding of the heteroduplex by MutS in solution. The duplexes were labeled with both biotin and $^{32}P$. The solution binding study measured radioactivity bound, whereas the immobilized MutS binding study measured biotin bound.

Oligonucleotides were labeled with both biotin and $^{32}P$, as described in the previous examples, which did not affect either biotin or radioactivity detection.

The binding of $^{32}P$-labeled heteroduplexes to MutS in solution was tested in a standard filter binding assay essentially as described by Jiricny, J. et al., Nucl. Acids Res. 16:7843–7853 (1988). The oligonucleotides were labeled as above and annealed with a 10-fold excess of unlabeled "complementary" oligonucleotides to yield a homoduplex and a heteroduplex containing a single G//T mismatch. For this assay, 500 ng of MutS in reaction buffer (20 μl) was incubated for 30 minutes at room temperature with the two types of duplexes. The mixture was spotted onto pre-wet nitrocellulose filters, which were then washed 5 times with 2 ml reaction buffer by vacuum filtration and dried at 80° C. for 15 minutes. Each filter was placed in 3 ml scintillation fluid and the radioactivity determined by scintillation counting. Background cpm (no MutS) were subtracted from the cpm bound by MutS. Means of duplicate or triplicate determinations are shown below.

The results of the binding to MutS in solution are shown in Table II, below.

TABLE II

| Mismatch | DNA (ng) | Net CPM bound | Exp/Control |
|---|---|---|---|
| Control (G:C) | 0.1 | 80 | |
| | 1.0 | 242 | |
| | 10.0 | 1403 | |
| Exp (G//T) | 0.1 | 142 | 1.8 |
| | 1.0 | 1252 | 5.2 |
| | 10.0 | 7236 | 5.2 |

These results show about a 5-fold increase in mismatch binding compared to homoduplex binding.

The results of binding of the identical DNA preparations to MutS immobilized on nitrocellulose are shown in FIG. 8. These are the same G//T and G:C pairings used above. Immobilized MutS detected binding of G//T heteroduplexes down to levels of 16 pg DNA. Control G:C homoduplexes appeared to bind only to 10 ng DNA over the "no MutS" background. These results indicate an increase of about 500-fold in mismatch binding compared to homoduplex binding. These results were highly unexpected in view of what was known from the prior art, particularly in view of the low ratios generally obtained with soluble MutS. Other experiments have given ratios as high as 1000 (see, for example, FIG. 1).

It was concluded from these studies that an immobilized mismatch binding protein is about two to three orders of magnitude more sensitive than the same protein in soluble form in a method for detecting nucleotide mismatches and thereby, for detecting mutations, heterozygosity, and allelic variants.

EXAMPLE VI

Removal of Mismatch Containing DNA from a PCR Amplified Sample

Two types of PCR products were examined. Both homozygous and heterozygous DNA 100 mers (SEQ ID NO:13, supra) and 230 mers were produced in PCR. For the heterozygous 230 mer, the template (DGK79) was human genomic DNA known to be heterozygous for a mutation (GCC to TCC, Gly to Ser, at codon 53) in exon 2 of the glucokinase gene (obtained from Dr. N. Cohen, CEPH, Paris, France. The corresponding homozygous template was human genomic DNA presumed to be homozygous in exon 2 of the glucokinase gene (obtained from Sigma Chemical Co.)

PCR amplification was performed using "Vent" polymerase ($exo^+$) from Thermococcus litoralis (purchased from New England Biolabs). The primers for the 230 mers were:
Primer #1: 5'(biotin)-GAAGGTGATGAGACGGAT [SEQ ID NO:16]
Primer #2: 5'-CCCAGGAGATTCTGTCTC [SEQ ID NO:17]
The primers for the 100 mers were SEQ ID NO:14 and SEQ ID NO:15 (supra).

PCR mixtures (100 μl) each contained: 20 mM Tris-HCl pH 8.8, 10 mM KCl, 2 mM $MgSO_4$, 10 mM $(NH_4)_2SO_4$, 0.1% Triton X-100, 0.25 mM dNTPs, 0.2 μM primer #1, 0.2 μM primer #2, 200 ng template DNA, 2 units DNA polymerase. 30 cycles were performed as follows: Denaturation: 1 min., 94° C. Annealing: 1 min., 3 cycles 64° C., 3 cycles 62° C., 3 cycles 60° C., 3 cycles 58° C., 3 cycles 56° C., 15 cycles 54° C. Extension: 2 min., 72° C. Primers were removed with QIA quick spin columns (Quigen). PCR products were eluted in 10 mM Tris-HCl pH 8.0 and were adjusted to 0.1M NaCl. The additional denaturation and reannealing was done under the following conditions: 100° for 4 min, 50° for 60 min, 75° for 4 min, 50° for 30 min and cooling in a block overnight to room temperature.

The cleanup procedure was carried out at room temperature. The reaction buffer described above (see Examples I and II) was used in the MutS immobilized binding assay described above.

The clean-up was performed by flowing DNA through MutS which had been immobilized on Millipore Immobilon P Multi-screen plates (MAIP N45). The plates had been prepared as follows:

1. Immobilon P plates were prepared according to manufacture's instructions.
2. 200 μl of a MutS solution (120 ng/μl) were added to wells and allowed to incubate for 5 min.
3. Fluid was pulled through by vacuum and collected in a standard 96 well plate.
4. The collected MutS solutions were reapplied twice more to the original wells as in step 3 for a total of 3 cycles of MutS binding to wells.
5. Wells were washed by applying and pulling through 3×200 μl reaction buffer, and the wash fluid was discarded.
6. 200 μl BSA blocking solution (1 μg/μl BSA, 200 μg/well) was added to wells, incubated 5 min and pulled through.
7. DNA (75 ng in 40 μl) was added and incubated for 60 min. with gentle shaking.
8. The solution was pulled through and collected ("first fraction"). 20 μl reaction buffer was added to each well, pulled through, and combined with the first fraction ("DNA Pool").
9. The DNA Pool of duplicate wells was combined to achieve sufficient quantity for detection. A PCR amplified DNA preparation (A) not subjected to the above clean-up procedure ("Pre-clean up") served as a control. An aliquot was removed for quantitation of DNA. The remaining material was divided into two groups. One aliquot was the "post cleanup" fraction (B). The other aliquot was subjected to denaturing and reannealing (fraction C).
10. DNA to be quantitated was measured using the DEAE/ethidium bromide method, against a DNA digest standard.
11. Equal quantities of Preparations A, B and C were tested in the immobilized MutS assay. The immobilized MutS was prepared and the assay performed essentially as described in Examples I and II, above.

The following results were obtained. Immobilized MutS removed a majority of mismatched DNA from both amplified heterozygous and amplified homozygous DNA samples. In the case of heterozygous DNA, denaturing and reannealing recovered signal equal to that of the DNA before cleanup. Little or no signal was recovered following denaturation and reannealing of homozygous DNA.

EXAMPLE VII

Detection of Functional Mismatch Binding Protein in Cell Extracts

Studies were done to evaluate the immobilized MBP assay for its utility in screening a cell extract for the presence of a MBP. This approach is based on the expectation that a biological fluid or cell extract containing a MBP would bind the appropriate heteroduplex in solution and prevent the heteroduplex from being recognized and bound by immobilized MutS.

1. Inhibition of Immobilized MutS Binding by Soluble MutS

Increasing amount of *E. coli* MutS (8–5000 ng) were mixed in solution with 10 ng of the heterozygous 30 mer (Bio-Het) having a G//T mismatch 5' Biotin- GCACCTGACTCCTG GGGAGAAGTCTGCCGT -3' (SEQ ID NO:1)
3'- CGTGGACTGAGGACTCCTCTTCAGACGGCA -5' (SEQ ID NO:3)

and the mixture was incubated at room temperature with gentle shaking for 15 min. This mixture was then assayed for binding to immobilized MutS as described in Examples I and II.

The results (FIG. 9, Panel B) indicate that inhibition of binding could be detected at 200 ng MutS and was complete at 5000 ng MutS.

2. Inhibition of Immobilized MutS Binding by HeLa Cell Extract

HeLa cell nuclear extract was purchased from Promega (Catalog No. E3091; HeLaScribe™ Nuclear Extract, Transcription Grade). Increasing amounts (1–20 μg) of the HeLa nuclear extract were mixed with 2 ng Bio-Het DNA and incubated for 2 hours with gentle shaking at room temperature. This mixture was tested as above for the binding of the DNA to immobilized MutS.

Figure 9A:
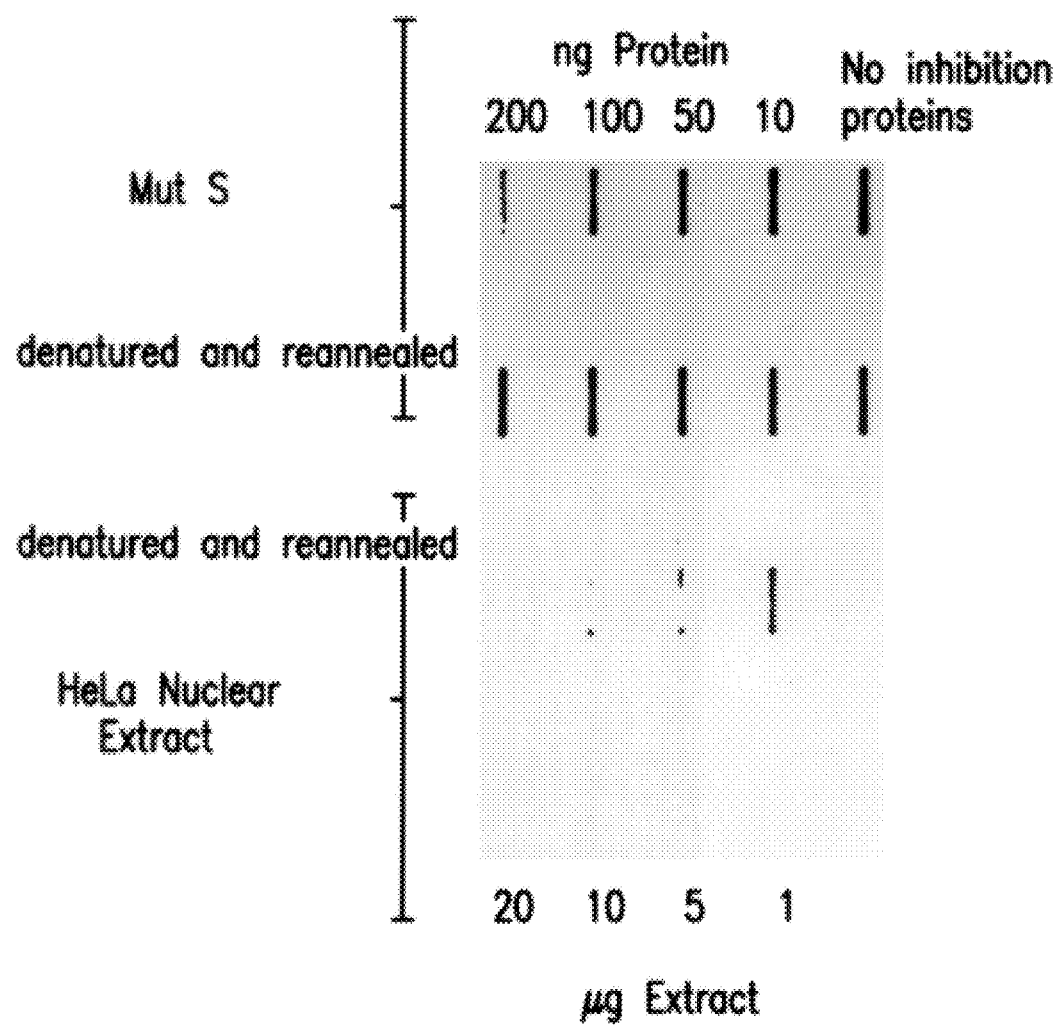
FIG. 9 shows the inhibition of the binding of mismatched DNA to MutS by soluble HeLa cell extract and soluble MutS. Panel A, upper half shows the inhibition by varying concentrations of soluble purified MutS of binding of 2 ng Bio-Het (G//T containing 30 mers). Panel A, lower half, shows inhibition by varying concentrations of HeLa cell nuclear extract. The inhibition by both inhibitors is shown to be reduced by denaturing conditions. Panel B shows the inhibition by MutS at varying concentrations (up to 5 μg) of binding of 10 ng of Bio-Het to 500 ng immobilized MutS.
Figure 9B:
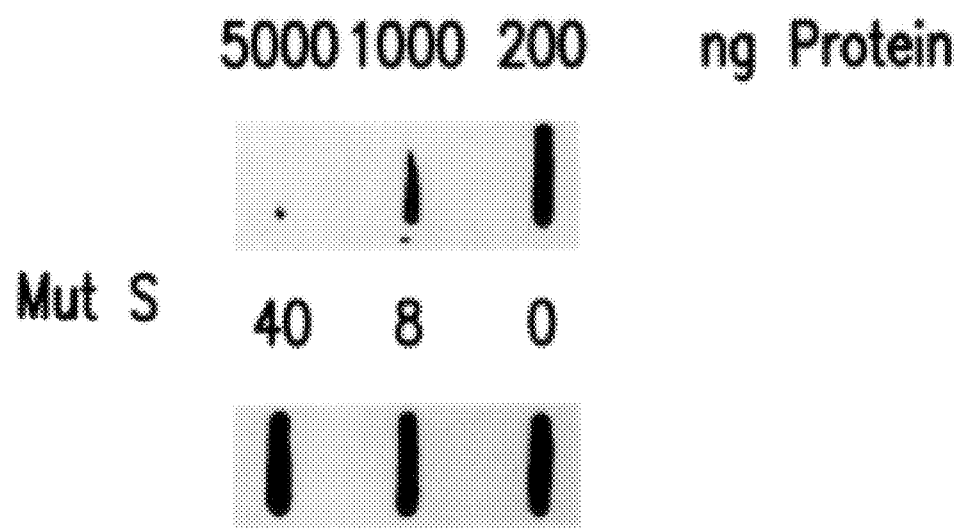

The results shown in FIG. 9, panel A, indicate that inhibition could be detected with 1 μg of extract and was complete at 5 μg.

To confirm that inhibition was due to DNA binding proteins and not to artifactual nuclease destruction of the DNA, the above mixtures were heated to 70° C. for 10 min. and cooled to room temperature for 30 min. This treatment is known to inactivate MutS and was intended to inactivate any other DNA binding proteins. The results shown in FIG. 9 indicate that DNA (the signal in the immobilized MutS assay) was recovered from each mixture. However, the signal was reduced in proportion to the amount of extract present, indicating that both nuclease and DNA binding activities are present in the extract.

EXAMPLE VIII

Self-Annealing of Triplet Repeat Sequences

Figure 10:
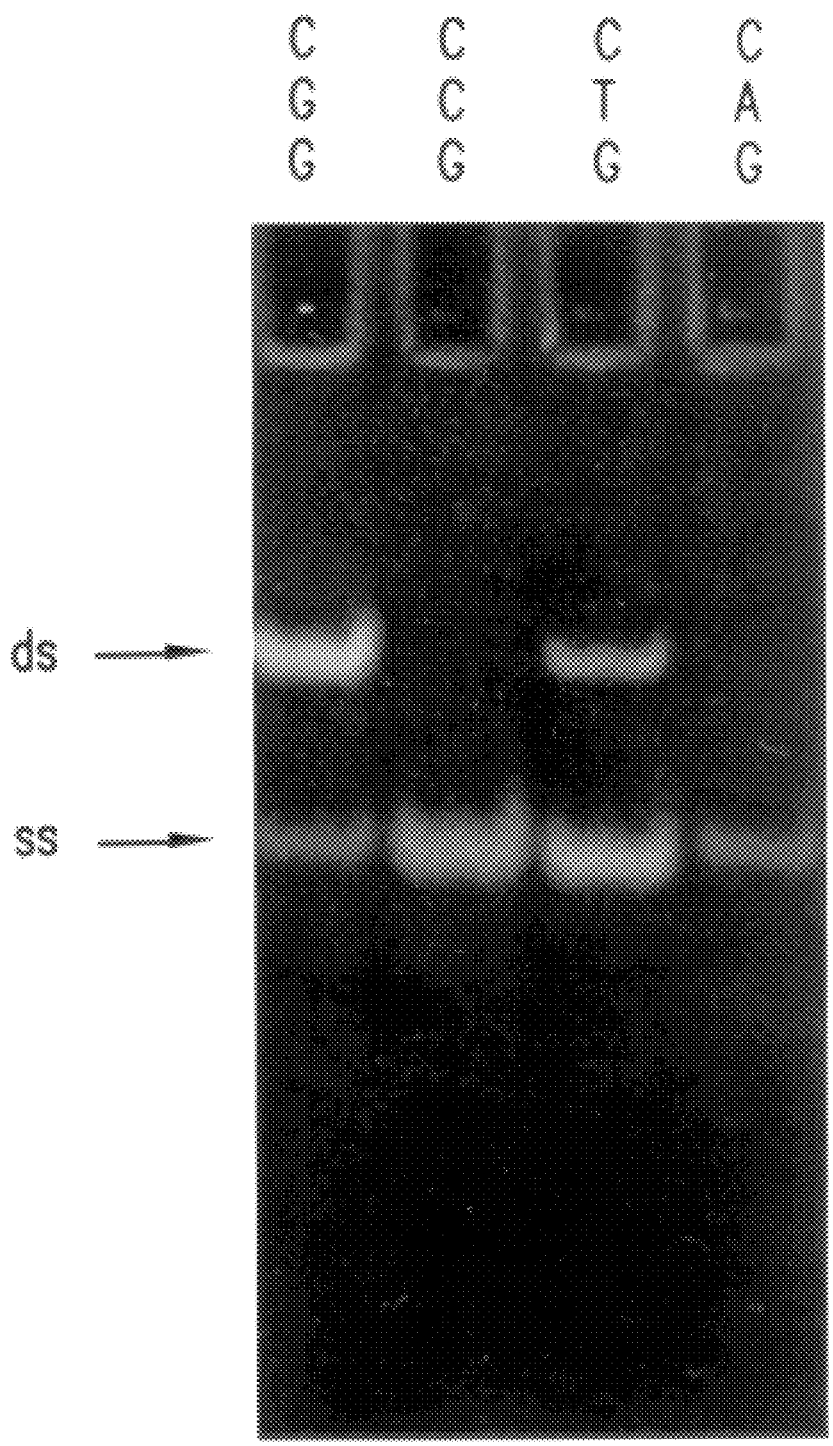
FIG. 10 shows the results of polyacrylamide gel electrophoresis of $(CXG)_{10}$ oligonucleotides. ds—double stranded 30 mer. ss—single stranded 30 mer.

The ability of the triplet repeat sequences to form secondary structure was determined by self-annealing synthetic $(CXG)_{10}$ 30 mer oligonucleotides with each of the four bases in the middle (X) position, and examining their behavior in polyacrylamide gel electrophoresis FIG. 10.

DNA in 10 mM Tris-HCl, pH 7.4, 1 mM EDTA. was heated to 70° C. for 10 min., cooled 45 min to room temperature and then cooled to 4° C. DNA was stored at 4° C. A quantity of 80 ng DNA was loaded into each well of a gel apparatus in a volume of 5 μl consisting of 0.1 μl DNA solution, 4.1 μl of buffer (450 mM Tris-Borate, 1 mM EDTA) plus 0.8 μl of a 70% glycerol, 0.25% Bromophenol Blue solution. The gel was a 20% acrylamide/bis gel. The electrophoresis was performed at 75 volts for 2 hours at 4° C. and the gel stained with ethidium bromide. The results are shown in FIG. 10. Differential staining of single stranded oligonucleotides is presumably a result of oligonucleotide-dependent differences in the extent of ethidium bromide intercalation.

The results indicate that the formation of secondary structure is dependent on the nature of the center mismatched base pair. The CGG and CTG repeats self-annealed to form a duplex structure, whereas the CCG and CAG repeats did not.

EXAMPLE IX

Binding of Triplet Repeats to Immobilized MutS

The ability of the triplet repeat sequences to form secondary structure was further determined by assessing their interaction in binding assays with immobilized mismatch binding protein.

DNA was prepared as described in the Examples above. 500 ng E. coli MutS was bound to nitrocellulose as described above and the experiment carried out as in the previous Examples. The results are shown in FIG. 11. Self-annealed single stranded triplet repeat sequences of CGG and CTG formed double-stranded mismatch-containing DNA duplexes which were recognized by immobilized MutS. In contrast, immobilized MutS did not bind to CCG and CAG triplet repeat sequences under these conditions.

It is concluded that, with the triplet repeats used in these experiments, the density or frequency of mismatches prevents the formation of duplex structure in a mismatch-dependent fashion. However, once a duplex is formed, immobilized MutS appears to recognize the mismatches in that structure despite their density.

The results shown in Examples VI and VII support the notion that repeat blocks of unpaired sequences of the type CGG and CTG (but not CCG or CAG) can form stable hairpin secondary structures.

EXAMPLE X

Instructions for a Preferred Assay for Detection of Mutation, Heterozygosity or Polymorphism All steps are performed at room temperature.

1. Prepare MutS reaction buffer by adding 100 ml of 10× reaction buffer (200 mM Tris-HCl pH 7.6, 50 mM $MgCl_2$, 1 mM DTT, and 0.1 mM EDTA) to 900 ml $ddH_2O$. Clarify with a 0.22 $\mu$m filter.

2. Cut nitrocellulose and 3 fiber pads (GB002 Schleicher & Schull) to fit within depression of Hoefer PR648 slot blot apparatus.

3. Float nitrocellulose on surface of a tray of reaction buffer for 2 minutes, then immerse by shaking. Keep immersed for 5 min.

4. Prepare MutS protein. Dilute in reaction buffer to 500 ng/20 $\mu$l. Vortex to mix.

5. Assemble slot blot apparatus, pouring off buffer squeezed from fiber pads. Pipet 100 $\mu$l of reaction buffer to all wells and pull through completely with vacuum.

6. Apply MutS solution, 20 $\mu$l (500 ng) to each well. Add equal volume of reaction buffer to "no MutS" wells. Incubate 20 min.

7. Prepare 3% HRP-free BSA (ICN) in reaction buffer. 30–40 ml are necessary for a full assay. Clarify with a 0.45 $\mu$M filter.

8. Pipet 200 $\mu$l of BSA to all wells. Incubate 1 hour, then pull through with vacuum.

9. Prepare DNA load samples. Use biotin labeled heteroduplex 30 mer (Bio-het) as positive control, and biotin labeled homoduplex 30 mer (Bio-homo) as a negative control. 1 or 5 ng are good control quantities. Dilute DNA in 3% HRP-free BSA, to 20 $\mu$l load volume.

10. Add DNA in 20 $\mu$l. Incubate 30 min.

11. Flick any residual DNA solution out of apparatus. Do not pull through. Wash 5×150 $\mu$l with reaction buffer, flicking each time.

12. Add 100 $\mu$l of 0.05 $\mu$g/ml streptavidin-HRP in 3% HRP-free BSA to each well. Incubate 20 min.

13. Flick off streptavidin-HRP solution. Wash 5×150 $\mu$l with reaction buffer, flicking each time. After last wash apply vacuum to pull through any residual liquid. Disassemble apparatus and transfer nitrocellulose to a tray containing 50 ml of reaction buffer. Immerse, pour off buffer, and add an additional 50 ml of reaction buffer, being careful not to pour buffer directly onto nitrocellulose. Repeat to wash a total of 5 times.

The following two steps, (14 and 15) are performed using the Enzygraphic web method. The IBI Enzygraphic™ Web is a support polymer coated with the detection system required to detect enzyme activity (in this case, peroxidase). The Web is similar to autoradiography film in principle, structure and use, though it differs in that it detects peroxidase-linked probes under ordinary room light. The Web is a general peroxidase detection system useful to localize peroxidase labels in a variety of situations, including visualization of proteins on Western transfers and is various other forms of nucleic acid hybridization and DNA sequencing (whenever peroxidase-linked probes are used).

In the current embodiment, when the coated surface of the Web and the peroxidase-linked probe are brought together on a blot, a characteristic blue band rapidly forms within seconds and peaks within minutes at the location of the probe/target complex. Rapid and sensitive detection occurs via an electron transfer process initiated by peroxidase to the unique Web detection system.

14. Blot nitrocellulose dry. Apply 25 mls of 0.05% Tween in 10 mM Tris-Cl, 1 mM EDTA, pH 8.0. Gently shake for 3 min. Pour off Tween, rinse 4×50 mls with $ddH_2O$. Blot nitrocellulose keeping it damp. Apply Enzygraphic Web, frosted side down. Rub to be sure of proper contact. Develop for 3–6 min.

15. Carefully peel nitrocellulose from Web. Photocopy nitrocellulose, as color may change even after removal of web.

The following step (14) is performed in an alternative Enhanced Chemiluminescence assay, as described in the Examples above:

14. Blot nitrocellulose dry. Apply 10 ml ECL development solution (Amersham) for 1 min. Blot dry, place between overhead sheets, and expose to X-ray film for 15 to 300 seconds. 30 and 60 seconds are most typical exposure times.

EXAMPLE XI

A Kit for Mismatch Detection

An example of a preferred kit for use in the methods described herein, sufficient to perform 100 assays, comprises the following components.

1. Cardboard Box, 5×6×4 inches, with custom insert
2. E. coli MutS, 50 $\mu$g packaged in a 1.6 ml conical tube
3. BSA: 2 g HRP-free BSA in 4 ml Kimble glass vial
4. "Het", 100 ng, DNA heteroduplex 30 mer with G-T mismatch, packaged in 0.5 ml. eppendorf tube
5. "Homo", 100 ng, DNA homoduplex (perfectly matched) 30 mer, packaged in 0.5 ml eppendorf tube
6. Streptavidin, 0.5 $\mu$g, conjugated with HRP, packaged in 0.5 ml eppendorf tube
7. 2 sheets Enzygraphic web (Kodak, Catalog No. 2K0750)
8. 2 sheets BA-85 nitrocellulose (Schleicher and Schull)
9. 50 X "RXTN": 40 ml of 50-X Reaction buffer packaged in a 60 ml Nalgene vial
10. 6 Fiber pads (blotting paper pads), Schleicher & Schuell Catalog no. GB002

11. 2 small (2"×3") and 2 large (4"×6") locking plastic bags (C-Line, Polyzip)

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

I claim:

1. A method for detecting heterozygosity or the presence of a mutation or polymorphism in heterozygous form in a test DNA sample, which heterozygosity, mutation or polymorphism is the result of a deletion or addition of up to four nucleotides, which method comprises:
   (a) detectably labeling said test DNA any time prior to step (c) below;
   (b) denaturing double stranded DNA in said sample into single strands and allowing said single strands to reanneal into duplexes;
   (c) contacting said duplexes with immobilized E. coli MutS protein, a homologue thereof or a functional derivative of said MutS or of said homologue, under conditions in which heteroduplexes containing one to four unpaired bases bind to said immobilized protein, homologue or derivative; and
   (d) detecting any bound heteroduplexes of step (c), wherein the presence of bound heteroduplex DNA is indicative of the presence of said heterozygosity, mutation or polymorphism in said test DNA.

2. A method according to claim 1, wherein said test DNA in said sample is amplified prior to step (a).

3. A method according to claim 1 wherein said immobilized protein, homologue or derivative is immobilized to a solid support selected from the group consisting of natural cellulose, nitrocellulose or other modified cellulose, polystyrene, polypropylene, polyethylene, dextran, nylon, polyacrylamide, polyvinylidene difluoride, agarose and magnetic beads.

4. A method according to claim 1 wherein said detectably labeled DNA has a detectable label which is a chromogenic compound, a chemiluminescent compound, a bioluminescent compound, a fluorescent compound, a radiolabel or biotin.

5. A method for detecting any specific DNA sequence in a test DNA sample, which method comprises:
   (a) detectably labeling anytime prior to step (c) below,
      (i) test DNA in said sample, or
      (ii) an added DNA polynucleotide or oligonucleotide as recited in step (b), below, or
      (iii) both (i) and (ii);
   (b) denaturing double stranded DNA in said sample into single strands and allowing said single strands to anneal into duplexes in the presence of an added DNA polynucleotide or oligonucleotide having a sequence such that said added DNA forms a perfectly matched duplex with said specific sequence;
   (c) contacting said duplexes with immobilized E. coli MutS protein, a homologue thereof or a functional derivative of said MutS or of said homologue, under conditions in which heteroduplexes containing one to four unpaired bases bind to said immobilized protein, homologue or derivative; and
   (d) detecting bound heteroduplexes of step (c), wherein the absence of bound heteroduplexes is indicative of the presence of said specific sequence in said test DNA.

6. A method according to claim 5, wherein said sample DNA is amplified prior to step (b).

7. A method for detecting heterozygosity or the presence of a mutation or polymorphism in heterozygous form in a test DNA sample, which heterozygosity, mutation or polymorphism is the result of a deletion or addition of up to four nucleotides, which method comprises:
   (a) denaturing double stranded DNA in said sample into single strands and allowing said single strands to reanneal into duplexes;
   (b) contacting the denatured and reannealed duplexes of step (a) with E. coli MutS protein, a homologue thereof or a functional derivative of said MutS or of said homologue, immobilized to a sold support, either
      (i) in the presence of a detectably labeled double stranded DNA oligonucleotide containing one to four unpaired bases, wherein said oligonucleotide is capable of binding to said protein, homologue or derivative, or
      (ii) wherein said immobilized protein, homologue or derivative was previously allowed to bind to a detectably labeled double stranded DNA oligonucleotide containing one to four unpaired bases,
   under conditions in which heteroduplexes containing one to four unpaired bases bind to said immobilized protein, homologue or derivative; and
   (c) detecting the amount of bound detectably labeled oligonucleotide,
wherein a decrease in the amount of bound detectably labeled oligonucleotide is indicative of the presence of said heterozygosity, mutation, or polymorphism.

8. A method for detecting a homozygous or heterozygous mutation or a polymorphism in test DNA in a sample, which mutation or polymorphism is the result of a deletion or addition of up to four nucleotides, which method comprises:
   (a) denaturing double stranded DNA in said sample into single strands, and allowing said single strands to reanneal into duplexes in the presence of an added DNA polynucleotide or oligonucleotide having the wild type sequence for said mutation or lacking said polymorphism;
   (b) contacting the denatured and reannealed duplexes formed in step (a) with E. coli MutS protein, a homologue thereof or a functional derivative of said MutS or of said homologue, immobilized to a solid support, either
      (i) in the presence of a detectably labeled double stranded DNA oligonucleotide containing one to four unpaired bases, wherein said oligonucleotide is capable of binding to said protein, homologue or derivative, or
      (ii) wherein said immobilized protein, homologue or derivative was previously allowed to bind to a detectably labeled double stranded DNA oligonucleotide containing one to four unpaired bases prior to said contacting, under conditions in which heteroduplexes containing one to four unpaired bases bind to said immobilized protein, homologue or derivative; and (c) detecting the amount of bound detectably labeled oligonucleotide, wherein a decrease in the amount of bound detectably labeled oligonucleotide is indicative of the presence of said homozygous or heterozygous mutation or polymorphism in said test DNA of said sample.

9. A method according to claim 7, wherein said sample DNA is amplified prior to step (a).

10. A method according to claim 8, wherein said sample DNA is amplified prior to step (a).

11. A method according to claim 10, wherein said added DNA polynucleotide or oligonucleotide of step (a) is added prior to said amplifying step.

12. A method for detecting in a DNA sample specific sequences characterized in being rare or minority sequences, wherein said rare and minority sequences differ from the majority sequences of said DNA sample by one or more deletions or additions of one to four nucleotides, which method comprises:

(a) subjecting the DNA sample to conditions of denaturation followed by annealing, such that said rare or minority sequences pair with the majority sequences to form heteroduplexes containing one to four unpaired bases, thereby generating in said sample a mixture of perfectly matched duplexes and heteroduplexes;

(b) contacting the mixture of step (a) with immobilized *E. coli* MutS protein, a homologue thereof or a functional derivative of said MutS or of said homologue, under conditions in which said heteroduplexes formed in step (a) bind to said immobilized protein;

(c) separating any unbound DNA from said bound heteroduplexes; and (d) detecting bound heteroduplexes, wherein the presence of bound heteroduplexes is indicative of the presence of said specific sequences in said sample DNA.

13. A method for screening a test DNA sample for the presence of a mutation or polymorphism in a specific known region, wherein said mutation or polymorphism: (i) results from a deletion or addition of up to four nucleotides, and (ii) results in formation of a heteroduplex when a mutant or polymorphic DNA strand is paired with a DNA strand of known sequence, which heteroduplex is bound by *E. coli* MutS protein, a homologue thereof or a functional derivative of said MutS or of said homologue, said method comprising:

(a) detectably labeling said test DNA any time prior to step (c) below;

(b) denaturing double stranded DNA in said sample into single strands and allowing said single strands to reanneal into duplexes;

(c) contacting said DNA duplexes with immobilized *E. coli* MutS protein, a homologue thereof or a functional derivative of said MutS or of said homologue, under conditions in which heteroduplexes containing one to four unpaired bases bind to said protein, homologue or derivative; and (d) detecting any bound heteroduplexes of step (c), wherein the presence of bound heteroduplex DNA is indicative of the presence of said mutation or polymorphism in said specific known region of said test DNA.

14. A method for screening a test DNA sample for the presence of a homozygous or heterozygous mutation or polymorphism in a specific region, wherein said mutation or polymorphism: (i) results from a deletion or addition of up to four nucleotides, and (ii) results in formation of a heteroduplex when a mutant or polymorphic DNA strand is paired with a DNA strand of known sequence, which heteroduplex is bound by *E. coli* MutS protein, a homologue thereof or a functional derivative of said MutS or of said homologue, said method comprising:

(a) denaturing double stranded DNA in said sample into single strands and allowing said single strands to reanneal into duplexes in the presence of a detectably labeled DNA polynucleotide or oligonucleotide having the known sequence, resulting in the formation of detectably labeled DNA duplexes;

(b) contacting said detectably labeled DNA duplexes formed in step (a) with immobilized *E. coli* MutS protein, a homologue thereof or a functional derivative of said MutS or of said homologue, under conditions in which heteroduplexes containing one to four unpaired bases bind to said protein, homologue or derivative; and (c) detecting any bound heteroduplexes of step (c), wherein the presence of bound heteroduplex DNA is indicative of the presence of said mutation or polymorphism in said specific region of said test DNA.

15. A method for detecting in a test DNA sample a heterozygous sequence variant in a specific region having a known sequence, wherein said sequence variant differs from the known sequence by one or more deletions or additions of one to four nucleotides, which method comprises:

(a) digesting said test DNA with one or more restriction enzymes which result in the creation of a restriction fragment containing the site of said sequence variant;

(b) denaturing said restriction fragment into single strands and allowing said strands to anneal into duplexes;

(c) contacting said duplexes with immobilized *E. coli* MutS protein, a homologue thereof or a functional derivative of said MutS or of said homologue, under conditions in which heteroduplexes among said duplexes containing one to four unpaired bases bind to said protein, homologue or derivative; and (d) detecting said bound heteroduplexes, wherein the presence of said bound heteroduplexes is indicative of the presence of said heterozygous sequence variant in said test DNA.

16. A method for detecting a homozygous or heterozygous sequence variant in a specific region of a test DNA, wherein said sequence variant differs from a known DNA sequence by one or more deletions or additions of one to four nucleotides, which method comprises:

(a) digesting said test DNA with one or more restriction enzymes which result in the creation of a restriction fragment containing the site of said sequence variant;

(b) denaturing said restriction fragment into single strands and allowing said single strands to anneal into duplexes in the presence of an added DNA polynucleotide or oligonucleotide having the known sequence;

(c) contacting said duplexes with immobilized *E. coli* MutS protein, a homologue thereof or a functional derivative of said MutS or of said homologue, under condition in which heteroduplexes among said duplexes containing one to four unpaired bases bind to said protein, homologue or derivative; and (d) detecting said bound heteroduplexes, wherein the presence of said bound heteroduplexes is indicative of the presence of said homozygous or heterozygous sequence variant in said test DNA.

17. A method for detecting in a test DNA sample the presence of a heteroduplex having a deletion or addition of up to four nucleotides, which method comprises detecting the binding of DNA in said sample to *E. coli* MutS protein, a homologue thereof or a functional derivative of said MutS or of said homologue, which has been immobilized to a solid support, wherein the presence of DNA bound to the immobilized protein, homologue or derivative is indicative of the presence of said heteroduplex.

18. A method according to claim 15, wherein said bound heteroduplexes are amplified following binding.

19. A method according to claim 16, wherein said bound heteroduplexes are amplified following binding.

20. A method for detecting in a sample containing test DNA the presence of a specific known sequence in a selected region of a first allele of a multi-allelic system, or the presence of an unknown sequence, wherein said specific known sequence is characterized as differing from other sequences of known identity in said selected region of other known alleles of said multi-allelic system by one or more deletions or additions of up to four nucleotides, which method comprises:

(a) mixing a detectably labeled DNA probe with an excess of the test DNA under conditions of denaturation followed by annealing such that copies of the probe can form homoduplexes or heteroduplexes, which probe
   (i) is perfectly complementary to said specific known sequence of said first allele and forms detectably labeled homoduplexes when annealed with said specific known sequence, and
   (ii) forms detectably labeled heteroduplexes containing one to four unpaired bases when annealed with said other sequences of known identity in said selected region of other known alleles of said multi-allelic system;

(b) contacting the mixture formed in step (a) with an excess of immobilized *E. coli* MutS protein, or a homologue or functional derivative thereof, under conditions in which any detectably labeled heteroduplexes containing one to four unpaired bases formed in step (a) bind to said immobilized MutS protein, homologue or functional derivative;

(c) removing said immobilized protein, homologue or derivative along with any heteroduplexes containing one to four unpaired bases bound thereto from said test DNA, thereby leaving a remaining mixture; and (d) detecting the presence of said detectably labeled DNA probe in said remaining mixture of step (c), wherein the presence of said detectably labeled DNA probe indicates the presence in said sample containing test DNA of said specific known sequence or said unknown sequence.

* * * * *